(12) United States Patent
Lee et al.

(10) Patent No.: US 11,020,575 B2
(45) Date of Patent: Jun. 1, 2021

(54) IN VIVO DRUG DELIVERY DEVICES AND METHODS FOR DRUG DELIVERY

(71) Applicant: TARIS BIOMEDICAL LLC, Lexington, MA (US)

(72) Inventors: Heejin Lee, Bedford, MA (US); Emily Abbate, Nashua, NH (US); Sarah Hocking, Winchester, MA (US); Dennis Giesing, Lees Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 16/302,061

(22) PCT Filed: Feb. 1, 2018

(86) PCT No.: PCT/US2018/016463
§ 371 (c)(1),
(2) Date: Nov. 15, 2018

(87) PCT Pub. No.: WO2018/144738
PCT Pub. Date: Aug. 9, 2018

(65) Prior Publication Data
US 2019/0201329 A1  Jul. 4, 2019

Related U.S. Application Data

(60) Provisional application No. 62/480,744, filed on Apr. 3, 2017, provisional application No. 62/453,333, filed on Feb. 1, 2017.

(51) Int. Cl.
*A61K 9/00* (2006.01)
*A61M 31/00* (2006.01)
*A61M 37/00* (2006.01)

(52) U.S. Cl.
CPC ......... *A61M 31/002* (2013.01); *A61K 9/0004* (2013.01); *A61K 9/0034* (2013.01);
(Continued)

(58) Field of Classification Search
CPC . A61K 9/0034; A61K 9/0004; A61M 31/002; A61M 31/007; A61M 31/00;
(Continued)

(56) References Cited

U.S. PATENT DOCUMENTS

| 4,210,139 A | 7/1980 | Higuchi |
| 4,657,536 A | 4/1987 | Dorman |

(Continued)

FOREIGN PATENT DOCUMENTS

| WO | 2012/96985 A1 | 7/2012 |
| WO | 2015/026813 A1 | 2/2015 |

OTHER PUBLICATIONS

International Search Report and Written Opinion for PCT/US2018/016463, dated May 2, 2018 (18 pages).

*Primary Examiner* — Jenna Zhang
(74) *Attorney, Agent, or Firm* — Eversheds Sutherland (US) LLP

(57) ABSTRACT

Drug delivery devices and methods of administering drugs to patients are provided. A device (50) includes a reservoir (60) containing a drug (58). The reservoir (60) is defined by a wall (64) having a water-permeable portion, such that the water-permeable portion permits water to enter the device (50) and contact the drug (58). A restraining plug (56) closes off an opening of the device (50) such that transient microchannels (62) form between an elastic portion (54) of the device (50) and the restraining plug (56), upon the generation of a sufficient pressure within the reservoir (60), to release the drug (58) from the device (50). Methods of treating patients for neurogenic detrusor overactivity result- (Continued)

ing from a spinal cord injury and/or for idiopathic overactive bladder and urinary incontinence are also described.

47 Claims, 18 Drawing Sheets

(52) U.S. Cl.
CPC . *A61M 37/0069* (2013.01); *A61M 2205/0216* (2013.01); *A61M 2205/04* (2013.01)

(58) Field of Classification Search
CPC ...... A61M 31/0069; A61M 2205/0216; A61M 2205/04
See application file for complete search history.

(56) References Cited

U.S. PATENT DOCUMENTS

| | | | |
|---|---|---|---|
| 5,221,278 A | 6/1993 | Linkwitz et al. | |
| 5,340,590 A | 8/1994 | Wong et al. | |
| 5,456,679 A | 10/1995 | Balaban et al. | |
| 5,681,584 A | 10/1997 | Savastano et al. | |
| 5,997,527 A * | 12/1999 | Gumucio | A61K 9/0004 424/424 |
| 6,217,906 B1 * | 4/2001 | Gumucio | A61K 9/0004 424/438 |
| 7,207,982 B2 | 4/2007 | Dionne et al. | |
| 7,241,457 B2 | 7/2007 | Chen et al. | |
| 8,167,836 B2 | 5/2012 | Lee et al. | |
| 8,343,516 B2 | 1/2013 | Daniel et al. | |
| 8,679,094 B2 | 3/2014 | Cima et al. | |
| 8,801,694 B2 | 8/2014 | Lee et al. | |
| 9,017,312 B2 | 4/2015 | Lee et al. | |
| 9,814,671 B2 * | 11/2017 | Lee | A61K 9/0004 |
| 2006/0106455 A1 * | 5/2006 | Furst | A61F 2/82 623/1.31 |
| 2006/0193892 A1 * | 8/2006 | Furst | A61F 2/91 424/426 |
| 2009/0149833 A1 * | 6/2009 | Cima | A61K 9/0024 604/517 |
| 2010/0003297 A1 | 1/2010 | Tobias et al. | |
| 2010/0330149 A1 * | 12/2010 | Daniel | A61K 9/0034 424/430 |
| 2010/0331770 A1 * | 12/2010 | Lee | A61K 9/0034 604/57 |
| 2011/0060309 A1 * | 3/2011 | Lee | A61K 9/0004 604/500 |
| 2011/0152839 A1 | 6/2011 | Cima | |
| 2011/0166554 A1 | 7/2011 | Alessi et al. | |
| 2011/0202036 A1 | 8/2011 | Boyko et al. | |
| 2011/0218488 A1 | 9/2011 | Boyko et al. | |
| 2012/0089121 A1 * | 4/2012 | Lee | A61M 31/002 604/517 |
| 2012/0089122 A1 | 4/2012 | Lee et al. | |
| 2012/0203203 A1 | 8/2012 | Lee et al. | |
| 2013/0158675 A1 * | 6/2013 | Hutchins, III | A61M 25/0017 623/23.66 |
| 2014/0276637 A1 | 9/2014 | Massey, Jr. et al. | |
| 2015/0119467 A1 * | 4/2015 | Himes | A61P 13/00 514/626 |
| 2015/0360012 A1 * | 12/2015 | Sansone | A61M 31/002 604/892.1 |
| 2016/0008271 A1 * | 1/2016 | Lee | A61M 31/00 604/517 |
| 2016/0199544 A1 * | 7/2016 | Lee | A61L 31/16 604/892.1 |

\* cited by examiner

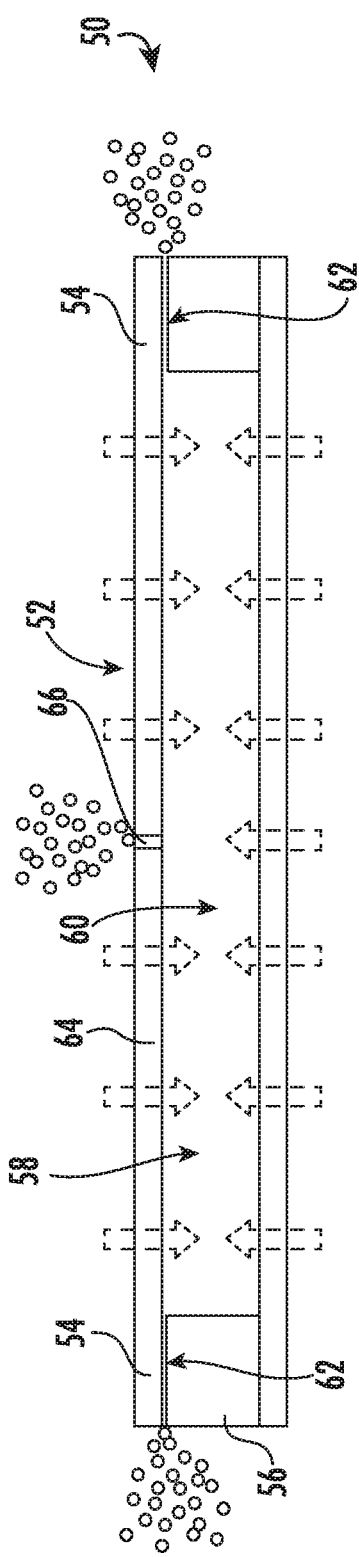
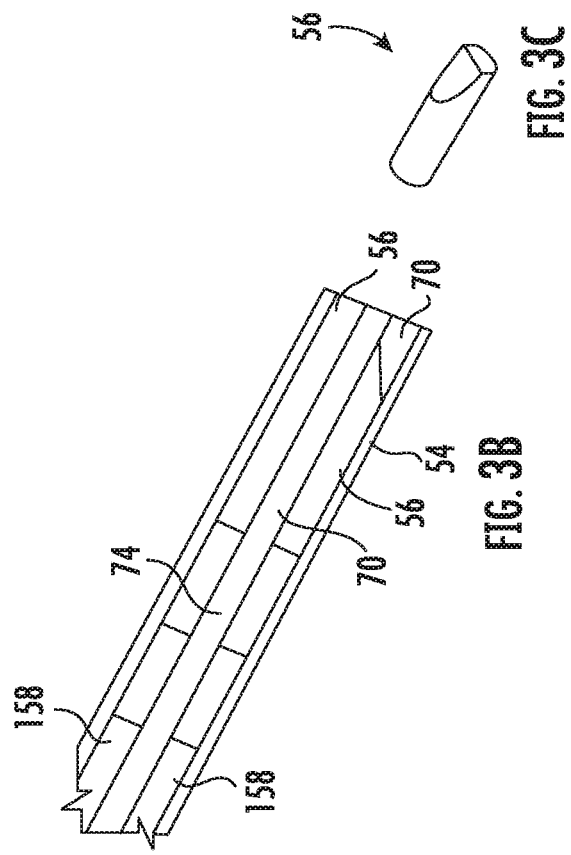
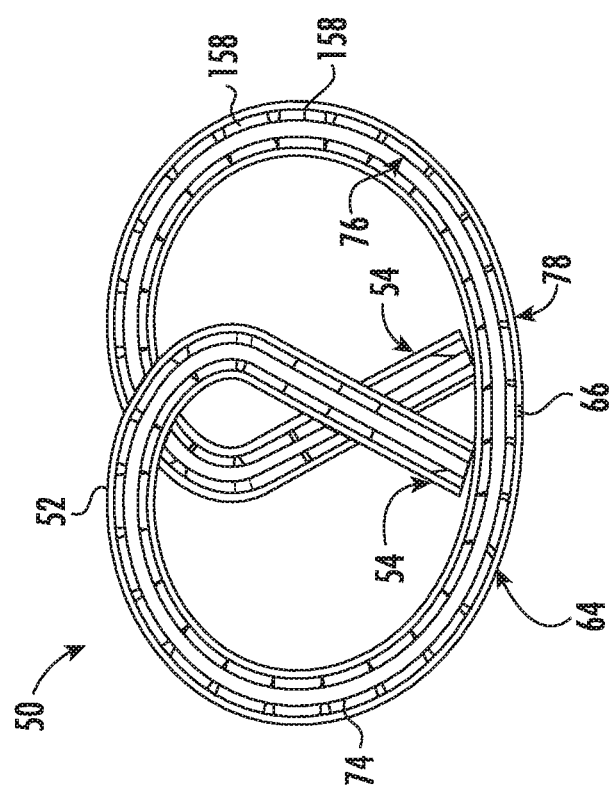
FIG. 2
FIG. 3B
FIG. 3C
FIG. 3A

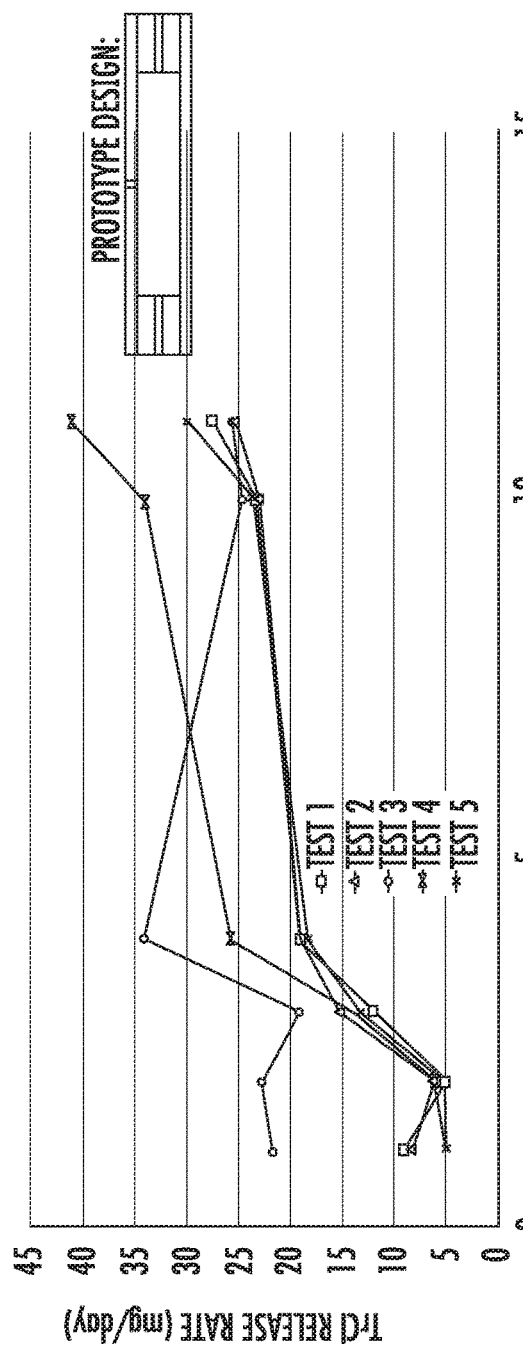
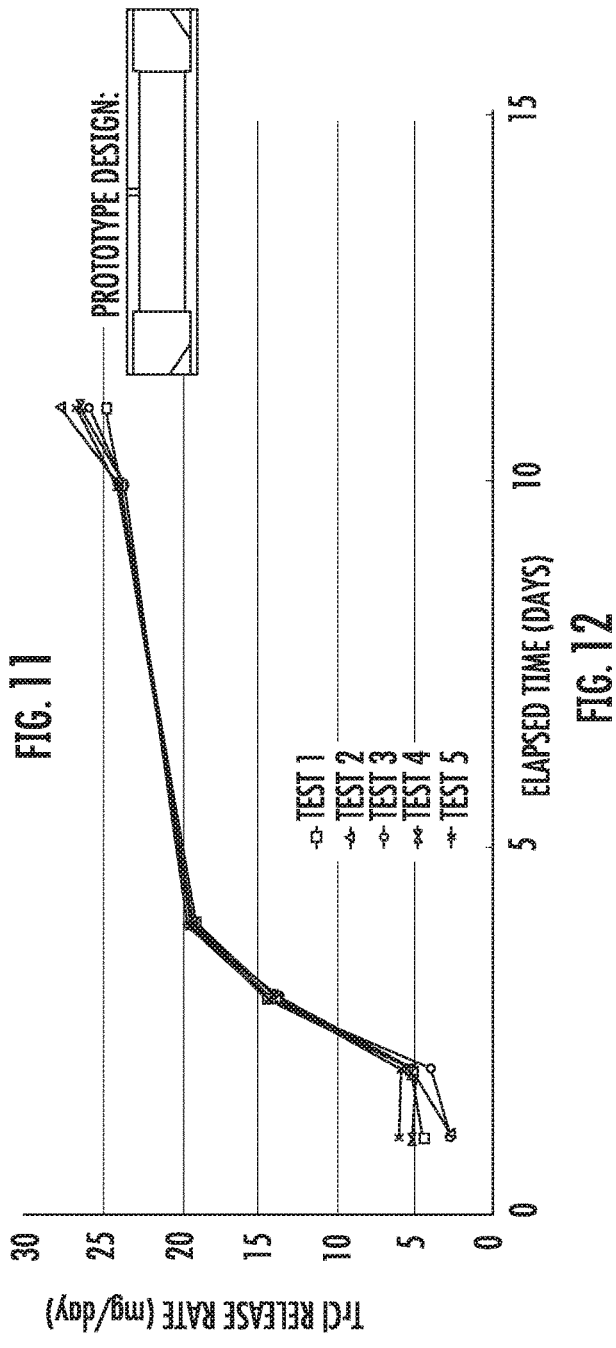

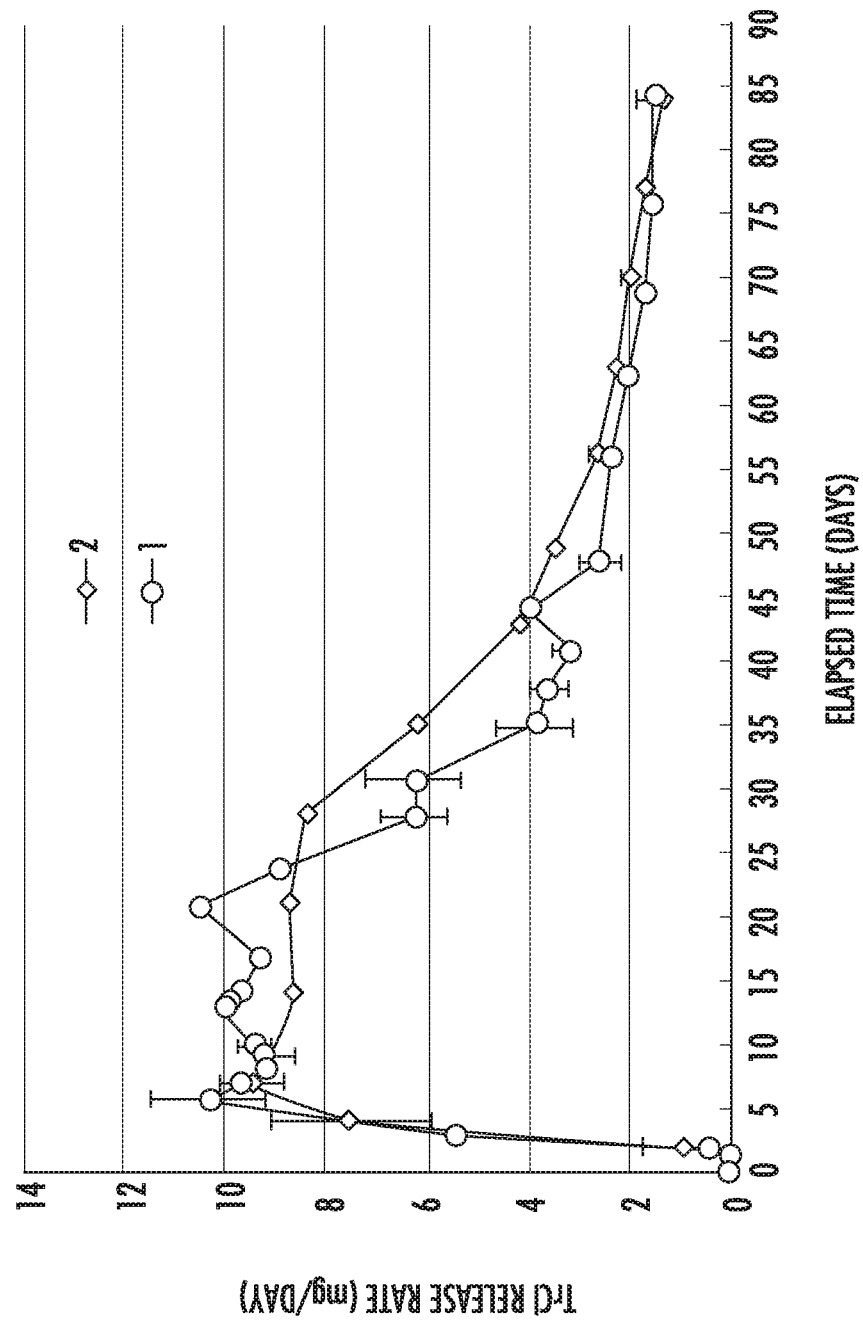

IN VIVO DRUG DELIVERY DEVICES AND METHODS FOR DRUG DELIVERY

CROSS-REFERENCE TO RELATED APPLICATIONS

This application is a U.S. national stage application of International Application No. PCT/US2018/016463, filed Feb. 1, 2018, which claims priority benefit of U.S. Provisional Applications No. 62/453,333, filed Feb. 1, 2017, and 62/480,744, filed Apr. 3, 2017, the disclosures of which are incorporated herein by reference.

BACKGROUND

This disclosure generally relates to medical devices deployable in vivo for controlled drug delivery, and more particularly relates to such devices having a water-permeable wall portion and one or more mechanisms for providing controlled drug release from the device.

Many current drug delivery devices rely on one or more orifices in the sidewall or end of the device, to permit the release of a drug therefrom. However, such orifices, especially those disposed in a sidewall of a device, may be susceptible to encrustation and clogging after the drug delivery device is deployed in a patient. A clogged orifice is undesirable because it often leads to less reproducible drug release, or it may prevent drug release entirely. Additionally, orifices disposed in ends of the device provide release only at the terminal portion of the device, which may not be desirable for all device configurations and drug formulations.

In other cases, a drug delivery device may not have a release orifice and release of drug is controlled by diffusion from a matrix material and/or through a wall bounding a reservoir of the drug. Such configurations, which rely on diffusion, however, may limit the drug release kinetics that can be achieved and/or may limit the range of suitable materials of construction to ones that lack the desired biocompatibility, stability, sterilizability, and mechanical properties, including manufacturability, wall thickness, flexibility, etc.

Accordingly, a need exists for drug delivery devices that overcome one or more of these disadvantages. A need also exists to provide improved methods and drug delivery systems for treating patients with idiopathic overactive bladder and urinary incontinence and patients with neurogenic detrusor overactivity resulting from spinal cord injury.

SUMMARY

In one aspect, a drug delivery device is provided, including a body that has a wall bounding a reservoir defined within the body, the wall having at least one preformed through-hole disposed therein and having a water-permeable portion, the body including an elastic portion; a drug formulation which includes a drug, the drug formulation being disposed within the reservoir; and at least one restraining plug closing off an opening of the body and contacting the elastic portion of the body, the opening being in fluid communication with the reservoir, wherein the water-permeable portion of the wall is configured to permit water to enter the drug delivery device and contact the drug formulation located in the reservoir, wherein release of the drug from the device is controlled by (i) release of the drug through the at least one preformed through-hole in the wall, and (ii) release of the drug through the transient formation of one or more microchannels between the elastic portion of the body and the at least one restraining plug, extending to the opening, upon the generation within the reservoir of a hydrostatic pressure effective to form the one or more microchannels.

In another aspect, a drug delivery device is provided, including a tubular body that has a wall bounding a reservoir defined within the body, the wall having a water-permeable portion and an elastic portion having at least one preformed release port disposed therein; a drug formulation which includes a drug, the drug formulation being disposed within the reservoir, wherein the water-permeable portion of the wall permits water to enter the drug delivery device and contact the drug formulation located in the reservoir; and at least one restraining plug secured within the reservoir in contact with the elastic portion of the body and adjacent the at least one preformed release port, such that the at least one restraining plug controls release of the drug from the device, via the at least one preformed release port, by the transient formation of one or more microchannels between the elastic portion of the body and the at least one restraining plug, extending to the at least one preformed release port, upon the generation of a hydrostatic pressure within the reservoir effective to form the one or more microchannels.

In yet another aspect, methods of administering a drug to a patient using one of the above-described devices are provided, including inserting the drug delivery device into a lumen or body cavity of a patient; and permitting water influx into the reservoir to develop a pressure in the reservoir effective to cause the drug to flow from the reservoir and out of the device and into the lumen or body cavity.

In still yet another aspect, a method of treating a patient in need of treatment for neurogenic detrusor overactivity (NDO) resulting from a spinal cord injury (SCI) is provided, including locally administering an effective amount of trospium into the urinary bladder of the patient continuously over a treatment period of 30 to 60 days.

In still yet another aspect, a method of treating a patient in need of treatment for idiopathic overactive bladder (iOAB) and urinary incontinence is provided, including locally administering an effective amount of trospium into the urinary bladder of the patient continuously over a treatment period of 30 to 60 days.

BRIEF DESCRIPTION OF THE DRAWINGS

Referring now to the drawings, which are meant to be exemplary and not limiting, and wherein like elements are numbered alike. The detailed description is set forth with reference to the accompanying drawings illustrating examples of the disclosure, in which use of the same reference numerals indicates similar or identical items. Certain embodiments of the present disclosure may include elements, components, and/or configurations other than those illustrated in the drawings, and some of the elements, components, and/or configurations illustrated in the drawings may not be present in certain embodiments.

FIG. 2 is a cross-sectional side view of one embodiment of a device having a preformed sidewall orifice and two restraining end plugs.

FIG. 3A is a plan view of one embodiment of a device having a preformed sidewall orifice and two restraining end plugs.

FIG. 3B is a cross-sectional magnified view of one of the end plugs of FIG. 3A.

FIG. 3C is an exploded perspective view of the end plug of FIG. 3B.

FIG. 11 is a graph showing drug release rate over time for a drug delivery device tested in the Examples.

FIG. 12 is a graph showing drug release rate over time for a drug delivery device tested in the Examples.

FIG. 24 is a graph showing drug release rate over time for various drug delivery devices tested in the Examples.

DETAILED DESCRIPTION

Figure 1A:
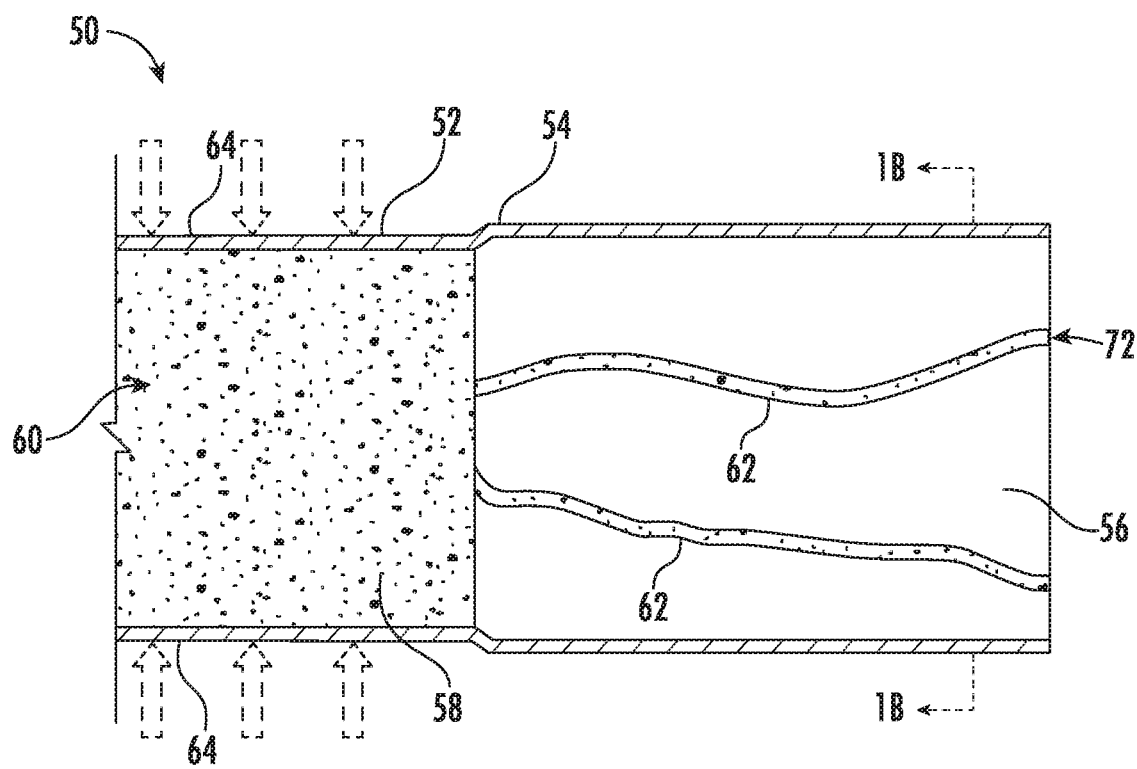
FIG. 1A is a cross-sectional side view of one embodiment of an elastic portion of a device containing a restraining end plug.
Figure 1B:
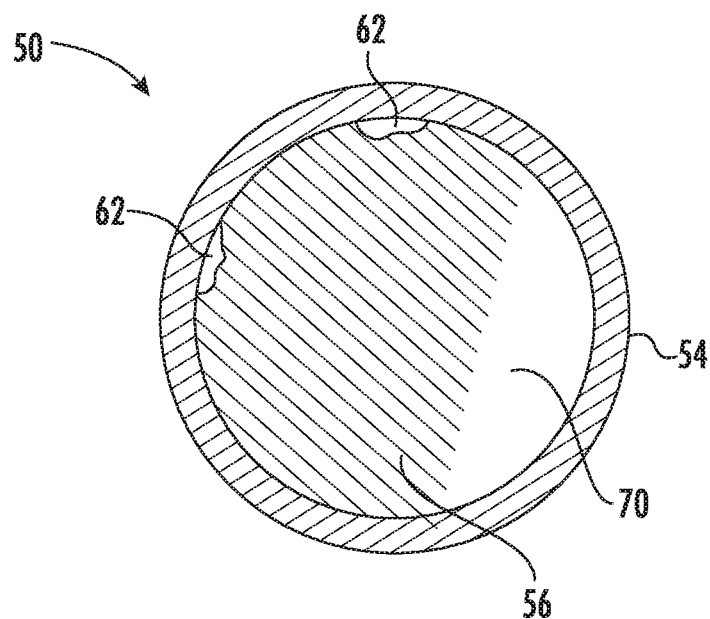
FIG. 1B is a cross-sectional end view of the embodiment of FIG. 1A.

Drug delivery devices 50 having a water-permeable wall portion 64 bounding a reservoir 60 (also referred to herein as a "reservoir lumen" or a "drug reservoir lumen") containing a payload 58, such as a drug formulation, are provided herein, along with methods for delivering the payload 58 from the device 50. As shown in FIG. 2, the water-permeable wall portion 64 may generally be configured to permit water to enter the device and contact the drug formulation (i.e., payload) 58 located in the reservoir 60, to facilitate release of the drug 58 from the device. For example, osmotically driven water influx into the reservoir 60 may generate a pressure within the reservoir 60 that drives release of the drug 58 from the reservoir 60 via one or more mechanisms. For example, in embodiments described herein, release of the drug 58 from the device may occur through one or more preformed sidewall orifices 66 (see FIG. 2) and/or through the transient formation of one or more microchannels 62 leading to a preformed release port 68 or other opening (see FIG. 9). In certain embodiments described herein, combinations of these release mechanisms are employed to provide the desired drug release profile and to overcome the disadvantages discovered in devices exclusively relying on one or more preformed orifices for drug release.

In particular, it has been discovered that implantable intravesical drug delivery devices in which preformed orifices in the side or end walls of the device are utilized for the release of drug from the device are susceptible to encrustation and clogging of the orifices following intravesical deployment, or implantation. Thus, in certain embodiments, as shown in FIG. 2, drug delivery devices 50 of the present disclosure contain one or more predefined orifices 66 in the sidewall or end of the device in combination with a one-way valve structure involving the transient formation of one or more microchannels 62 leading to a preformed release port or other opening, upon the generation of a hydrostatic pressure effective to form the one or more microchannels in the reservoir 60. For example, the generation of a hydrostatic pressure in the reservoir 60 that exceeds the threshold pressure for the transient formation of microchannels 62 may occur when the preformed orifice(s) 66 is partially or fully clogged or when release through the orifice(s) 66 does not occur quickly enough to relieve the hydrostatic pressure within the reservoir 60. In some embodiments, as shown in FIGS. 9 and 10, a preformed release port 68 in the sidewall or end of the device is provided in combination with a restraining plug 56 that blocks access to the release port 68, absent the generation of a hydrostatic pressure in the reservoir effective to form the one or more microchannels 62 extending to the release port 68.

It has been discovered that controlled release of drug can be achieved with devices having improved one-way valve release mechanisms, alone or in combination with other release mechanisms. For example, controlled release of drug can be achieved with the transient formation of microchannels through which a fluidized drug can be dispensed from a delivery device. The microchannels form at an interface of device components in response to a hydrostatic pressure developed in a drug reservoir. Drug delivery devices configured to induce and utilize such microchannels (i.e., which are distinct from preformed orifices) have been developed, which avoid or alleviate the potential problems associated with conventional drug release mechanisms, including precision miniature orifices that may increase component cost and the risk of clogging, or that are limited by diffusion through or from another material.

In embodiments, the drug delivery device 50 includes a device body 52 having at least one water-permeable wall portion 64 bounding a drug reservoir 60 defined within the body 52. A drug formulation 58 which comprises a drug is loaded into the defined drug reservoir 60. The body 52 includes an elastic portion 54 in fluid communication with the drug reservoir 60. The device 50 further includes a restraining plug 56 that contacts the elastic portion 54 of the body 52 and controls release of the drug 58 from the device 50 by the transient formation of one or more microchannels 62 between the elastic portion 54 of the body 52 and the at least one restraining plug 56.

The term "microchannels," as used herein, refers to a passageway or system of passageways through which drugs can exit the devices described herein. In embodiments, the microchannels form in response to hydrostatic pressure that accumulates in the water-permeable body due to osmotically driven water influx; when the hydrostatic pressure increases above a certain threshold, the microchannels form, thereby forcing at least a portion of drug out of the device and relieving the hydrostatic pressure accumulation in the drug reservoir. The microchannel may collapse at least partially as the hydrostatic pressure has been relieved. This process repeats itself until all or a substantial portion of the drug has been released, or the osmotically driven water influx is insufficient to continue the process.

The microchannels may form anywhere along the inner surface of the elastic portion of the water-permeable body, thereby significantly and beneficially reducing the likelihood of complete clogging—even when insoluble excipients are used in the drug formulation. Advantageously, the microchannels, unlike an orifice, may reduce or eliminate the potential risk of sudden drug discharge when the device is compressed or deformed. For example, when the drug delivery devices are surrounded by body fluid and disposed in an environment that exposes the devices to moderate external mechanical stress (such as during urination when the device is a deployed intravesical drug delivery device), drugs are less likely to be discharged through the microchannels.

Figure 1C:
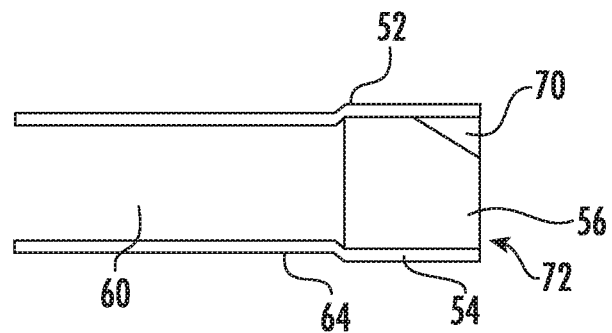
FIG. 1C is a cross-sectional side view of the device of FIG. 1A when the reservoir is not under an osmotic pressure.

FIGS. 1A-1D show one embodiment of the microchannels in a drug delivery device. Device 50 includes a body, or housing, 52 having an elastic portion 54 with a restraining plug 56 inserted into an opening in the body 52 such that the elastic portion 54 is positioned against (around) an outer surface of the restraining plug 56. As indicated by the dashed line arrows, water diffuses through a water-permeable wall 64 of the body 52 and enters the drug reservoir 60, forming fluidized drug 58, which for example may be an aqueous solution comprising the drug 58 initially loaded in the reservoir 60. Hydrostatic pressure in the reservoir 60 causes the fluidized drug 58 to be pushed out of the reservoir 60 between the elastic portion 54 and the restraining plug 56, through microchannels 62 that are formed therebetween, for example by elastic deformation of one or both of the interfacing surfaces. FIG. 1C illustrates the device in a state in which hydrostatic pressure in the reservoir has not reached the threshold such that any microchannels are formed between the elastic portion 54 and the restraining plug 56. In the embodiment illustrated in FIGS. 1A 1B, and 1D, the microchannel 62 is shown as forming between the reservoir 60 and the terminal (preformed) opening 72 of the device 50; however, as described below, in some embodiments, the device 50 is configured such that the microchannel 62 forms between the reservoir 60 and a release port 68 defined in the sidewall or a closed end of the device.

The devices, systems, and methods disclosed herein, build upon some features and aspects of the devices, systems and methods described in the following Patent Application Publications: U.S. 2016/0199544 (Lee et al.); U.S. 2012/0089122 (Lee et al.); U.S. 2012/0089121 (Lee et al.); U.S. 2011/0152839 (Cima et al.); U.S. 2010/0331770 (Lee et al.); U.S. 2010/0330149 (Daniel et al.); U.S. 2009/0149833 (Cima et al.); and U.S. 2007/0202151 (Lee et al.), which, in pertinent part, are incorporated by reference herein.

The Drug Delivery Device

Figure 4:
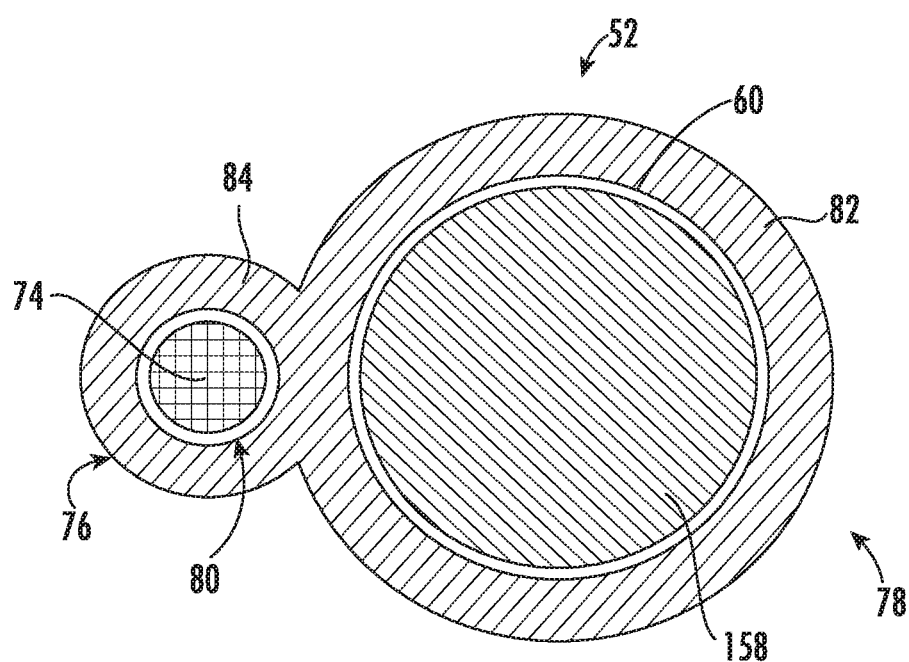
FIG. 4 is a cross-sectional end view of one embodiment of a drug delivery device.
Figure 7:
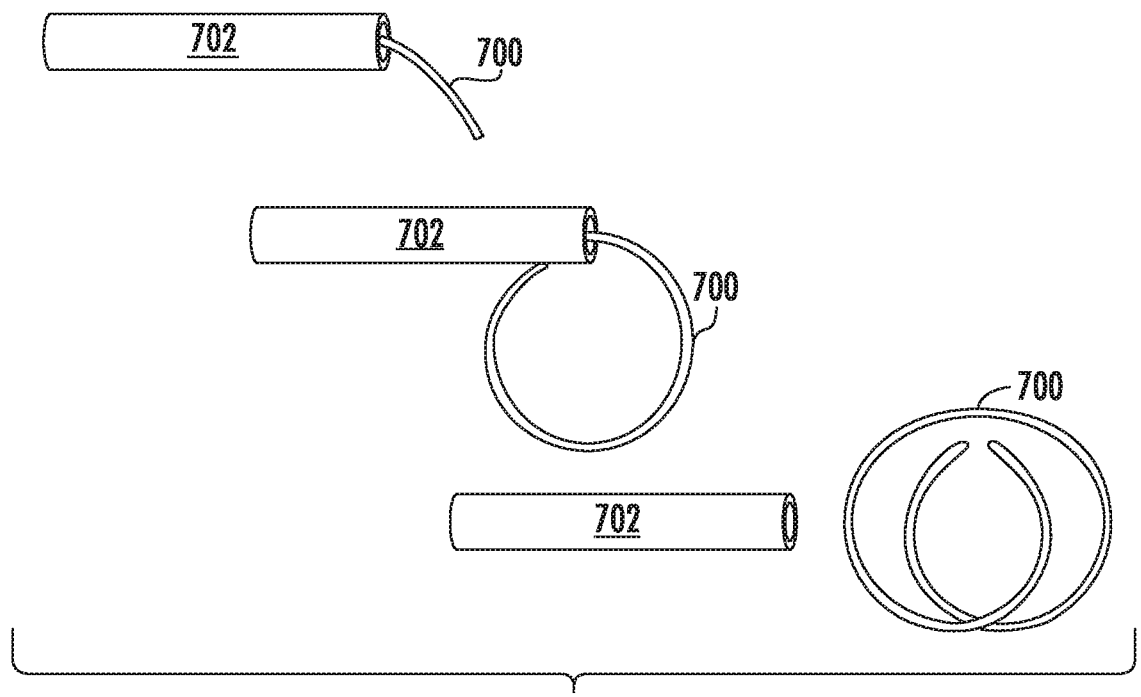
FIG. 7 illustrates deployment of a drug delivery device from a deployment instrument.

An embodiment of a drug delivery device is illustrated in FIGS. 3 and 4. The device includes a water-permeable body 52 having a drug reservoir portion 78 and a retention frame portion 76. As used herein, the term "drug reservoir portion" refers to the portion of the device that forms and defines the "drug reservoir" or "drug reservoir lumen". As such, these terms are used with reference to the same or similar and overlapping features of the devices. In FIG. 3A, the device 50 is shown in a relatively expanded shape suited for retention in the body, e.g., in the urinary bladder. As shown in FIG. 7, the device 700 may also be disposed in a relatively lower-profile shape for deployment through the channel of a deployment instrument 702, such as a cystoscope or other catheter. Following deployment into the body, the device may assume the relatively expanded shape to retain the drug delivery device in the bladder, or other body cavity or lumen.

In some embodiments, the intravesical device comprises a deployment shape and a retention shape. For example, as shown in FIG. 7, the device 700 may be elastically deformable between a relatively straightened or uncoiled shape suited for insertion through a lumen into the bladder of the patient (the deployment shape) and a retention shape suited to retain the device within the bladder. For the purposes of this disclosure, the term "retention shape" generally denotes any shape suited for retaining the device in the bladder, including but not limited to a coiled or "pretzel" shape. A pretzel shape is shown in FIG. 3A. The retention shape enables the device to resist becoming entrained in urine and excreted when the patient voids. The terms "relatively expanded shape", "relatively higher-profile shape" may be used interchangeably with "retention shape." Similarly, the term "relatively lower-profile shape" may be used interchangeably with "deployment shape" and generally denote any shape suited for deploying the drug delivery device into the body, including the linear or elongated shape shown in FIG. 7 that is suited for deploying the device through the working channel of a catheter, cystoscope, or other deployment instrument positioned in a lumen of the body, such as the urethra. In embodiments, the drug delivery device may naturally assume the relatively expanded shape and may be elastically deformed, either manually or with the aid of an external apparatus, into the relatively lower-profile shape for insertion into the body. Once deployed the device may spontaneously or naturally (e.g., elastically) return to the initial, relatively expanded shape for retention in the body. In some embodiments, the device behaves like a spring, deforming in response to a compressive load (e.g., deforming the device into a deployment shape) but spontaneously returning to a retention shape once the load is removed. In some embodiments, this shape changing functionality of the intravesical device is provided by including a shape retention frame (i.e., a "retention frame") in the device, as described hereinbelow.

In the illustrated embodiment of FIG. 4, the drug reservoir and retention frame portions 78, 76 of the drug delivery device are longitudinally aligned and are coupled to each other (or integrally formed together) along their length, although other configurations are possible. For example, the drug reservoir portion 78 may be attached to the retention frame portion 76 at discrete points but otherwise may be separate or spaced apart from the retention frame portion 76.

As shown in FIG. 4, the drug delivery device includes an elastic or flexible device body 52 that defines a drug reservoir lumen 60 and a retention frame lumen 80. The drug reservoir lumen 60 is designed to house a drug formulation, such as a number of solid drug tablets 158, to form the drug reservoir portion 78. The retention frame lumen 80 is designed to house a retention frame 74 to form the retention frame portion 76. The illustrated lumens 78, 76 are discrete from each other, although other configurations are possible.

As shown in the cross-sectional view of FIG. 4, the device body 52 includes a tube or wall 82 that defines the drug reservoir lumen 60 and a tube or wall 84 that defines the retention frame lumen 80. The tubes 82, 84 and lumens 60, 80 can be substantially cylindrical, with the drug reservoir lumen 60 having a relatively larger diameter than the retention frame lumen 80, although other configurations can be selected based on, for example, the amount of drug to be delivered, the diameter of the retention frame, and deployment considerations such as the inner diameter of the deployment instrument. The device body 52 may be formed integrally, such as via molding or extrusion, although separate construction and assembly of the tubes 82, 84 is possible. The wall 84 that defines the retention frame lumen 80 may extend along the entire length of the wall 82 that defines the drug reservoir lumen 60, so that the retention frame lumen 80 has the same length as the drug reservoir lumen 60 as shown, although one wall may be shorter than the other wall in other embodiments. Further, the two walls 82, 84 are attached along the entire length of the device in the illustrated embodiment, although intermittent attachment can be employed. In one example, the wall 82 of the drug reservoir lumen 60 has an inner diameter of about 1.5 mm and an outer diameter of about 1.9 mm, while the wall 84 of the retention frame lumen 80 has an inner diameter of about 0.5 mm and an outer diameter of about 0.9 mm. In another example, the wall 82 of the drug reservoir lumen 60 has an inner diameter of about 2.16 mm and an outer diameter of about 2.56 mm. However, the inner and outer diameters of the wall 82 of the drug reservoir lumen 60 and the wall 84 of the retention frame lumen 80 may be any suitable diameter. The cross-sectional area of the entire body of the device 52 may be about 0.035 $cm^2$ or less. However, the cross-sectional area of the entire body of the device 52 may be any suitable dimension.

As shown in FIG. 3A, the drug reservoir lumen may be loaded with a number of drug units 158 in a serial arrangement. The drug units may be tablets, such as mini-tablets. For example, between about 10 and about 100 drug units may be loaded, such as between about 30 and about 70 drug units, or more particularly between about 50 and 60 drug units. However, essentially any number of drug units may be used, depending upon the sizes of the reservoir and the drug units. The drug reservoir lumen includes openings, which may be relatively circular openings at opposite ends of the drug reservoir lumen. These openings provide ingress for the drug units to be placed into the drug reservoir lumen during device loading and assembly.

Restraining plugs, as described herein, may be disposed in the reservoir through the terminal openings of the device. The restraining plug and elastic portion may be disposed at any suitable position along the length of the drug delivery device. In certain embodiments, as described herein, a restraining plug may be disposed at or near the terminal end of the device. In other embodiments, a restraining plug may be disposed at or near the central portion of the device. In one embodiment, one of the terminal device openings has a restraining plug, and the opposed opening is sealed with a plug or other material that does not permit the formation of microchannels.

Figure 1D:
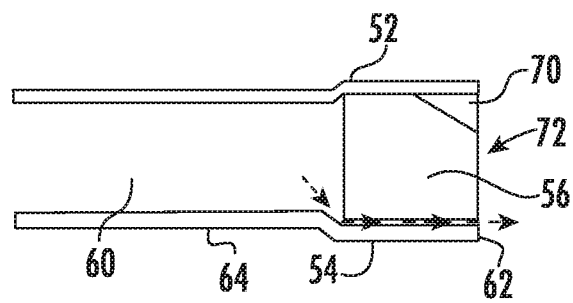
FIG. 1D is a cross-sectional side view of the device of FIG. 1A when the reservoir is under an osmotic pressure.
Figure 9A:
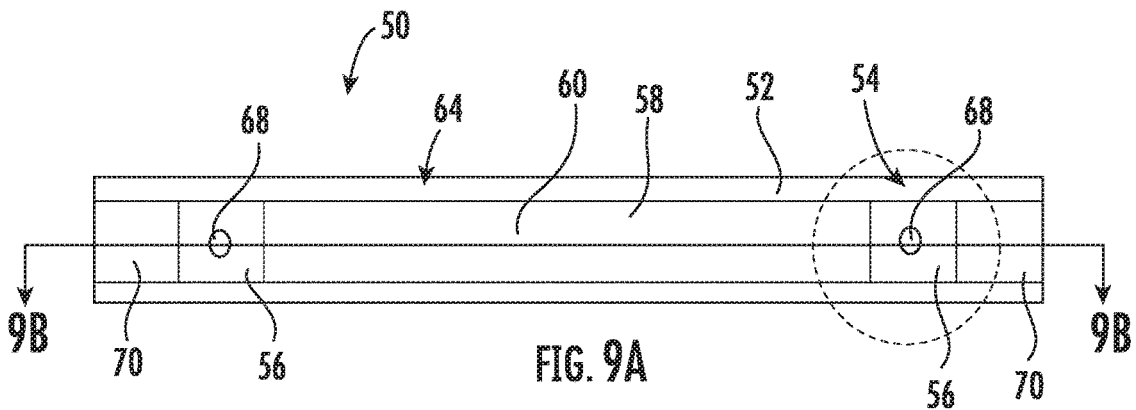
FIG. 9A is a plan view of one embodiment of a drug delivery device having restraining plugs and a preformed release port.
Figure 10A:
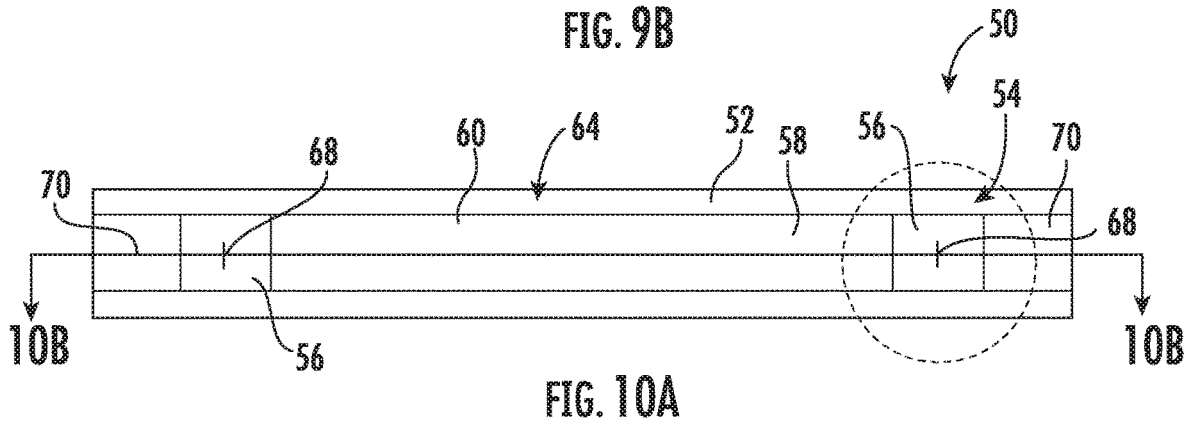
FIG. 10A is a plan view of one embodiment of a drug delivery device having restraining plugs and a preformed release port.

In some instances, as shown in FIGS. 1C and 1D, each of the restraining plugs 56 may, as described herein, have an outer diameter that is larger than the inner diameter of the drug reservoir lumen 60. In some embodiments, as shown in FIGS. 9A and 10A, the restraining plugs 56 may be secured within the drug reservoir lumen 60 at the terminal ends of the device 50, such that the terminal ends or openings of the device 50 are sealed, such as by an adhesive 70 or other suitable securement means. In other embodiments, as shown in FIGS. 1C-1D, the restraining plugs 56 may be secured within the drug reservoir lumen 60 by an adhesive 70, but without sealing the lumen. In still other embodiments, the restraining plugs may be secured within the drug reservoir lumen by an external clamp disposed about the drug reservoir lumen. The restraining plugs may be secured within the drug reservoir lumen by any means disclosed herein or a combination thereof, as long as it permits the desired formation of microchannels.

In certain embodiments, each of the restraining plugs may include a cavity for receiving an end portion of the retention frame. In some cases, a number of restraining plugs can be positioned in the openings or elsewhere along the length of the device. The restraining plugs may be silicone plugs, ethylene vinyl acetate plugs, or a combination thereof. In embodiments where one of the restraining plugs is omitted, the opening without the restraining plug is closed with any other suitable biocompatible material. In one example, the material is an adhesive substance that is placed in the drug reservoir lumen in workable form and cures therein. In some embodiments, a restraining plug is inserted into an opening of the drug reservoir lumen, and the other opening of the drug reservoir lumen is sealed with an adhesive. In other embodiments, both ends of the drug reservoir lumen may be sealed and one or more restraining plugs may be located within the device near the sealed ends or spaced away from the sealed ends.

As shown in FIG. 4, the retention frame lumen 80 is loaded with the retention frame 74, which may be an elastic wire. The retention frame 74 may be configured to return spontaneously to a retention shape, such as the illustrated example "pretzel" shape or another coiled shape, such as those disclosed in the patent application publications identified above and incorporated herein by reference. In particular, the retention frame 74 may retain the device in the body, such as in the bladder. For example, the retention frame 74 may have an elastic limit and modulus that allows the device 50 to be introduced into the body in a relatively lower-profile shape, permits the device to return to the relatively expanded shape once inside the body, and impedes the device from assuming the relatively lower-profile shape within the body in response to expected forces, such as the hydrodynamic forces associated with contraction of the detrusor muscle and urination. Thus, the device may be retained in the body once deployed, limiting or prevent accidental expulsion.

The material used to form the device body 52, at least in part, may be elastic or flexible to permit moving the device between deployment and retention shapes. When the device is in the retention shape, the retention frame portion 76 may tend to lie on the interior side of the drug reservoir portion 78, although the retention frame portion 76 can be positioned inside, outside, above, or below the drug reservoir portion 78 in other cases. At least a portion of the material used to form the device body 52 also is water-permeable so that solubilizing fluid (e.g., urine or other bodily fluid) can enter the drug reservoir 60 to solubilize the drug units 158 once the device is deployed. For example, silicone, ethylene vinyl acetate (EVA), thermoplastic polyurethanes, or another biocompatible elastomeric material may be used to form the device body.

In one embodiment in which the drug delivery device is designed to be inserted in the bladder, the drug delivery device is designed to be inserted into (and optionally retrieved from) the bladder through the urethra cystoscopically. Thus, the device may be sized and shaped to fit through a narrow tubular path of a deployment instrument, such as a catheter or cystoscope.

The exact configuration and shape of the drug delivery device may be selected depending upon a variety of factors including the specific site of deployment, route of insertion, drug, dosage regimen, and therapeutic application of the device. The design of the device may minimize the patient's pain and discomfort, while locally delivering a therapeutically effective dose of the drug to a tissue site (e.g., urothelial tissue) in a patient.

The Device Body/Drug Reservoir Portion

As shown in FIGS. 1-3, 9, and 10, the drug delivery device 50 has a body 52, e.g., a housing, that has a drug reservoir 60, which includes a water-permeable wall 64, and that includes an elastic portion 54 for engagement with the one or more restraining plugs 56. The drug reservoir 60 is at least partially defined by the water-permeable wall 64. That is, the device includes a "water-permeable body," which, as the phrase is sometimes used herein, includes any structure having at least a portion that is water-permeable. In embodiments, the water-permeable body is made entirely from a water-permeable material. In other embodiments, the water-permeable body is made from a water-permeable material and a non-water-permeable material. In further embodiments, the water-permeable body is made from a material having at least one water-permeable portion and at least one non-water-permeable portion. As used herein, a wall or material is "water-permeable" when it permits a fluid to enter the drug delivery device, e.g., by transwall diffusion, and contact the drug formulation located in a reservoir within the device body.

The body 52 of the drug delivery devices 50 described herein also includes at least one elastic portion 54. The elastic portion 54 of the device body 52 may be the same as or distinct from the water-permeable portion 64 of the device body 52 described in the preceding paragraph. In certain embodiments, as shown in FIG. 1A, the restraining plugs 56 contact the at least one elastic portion 54 of the device body 52 to close off an opening the body, which the opening is in fluid communication with the drug reservoir 60 within the device, thereby enclosing the drug 58 within the drug reservoir 60.

In some embodiments, all of the elastic portions of the device body are contacted with restraining plugs that permit drug release as described herein. In other embodiments, one or more of the elastic portions of the device body are contacted with restraining plugs that permit drug release as described herein and the remaining elastic portions of the body are sealed by other suitable means, such as a cap, an adhesive, heat-sealing, soldering, solvent welding, or a combination thereof.

Generally, the length of the elastic portion should equal or exceed the length of the portion of the restraining plug that contacts the elastic portion of the device body, so that formation/use of the microchannels is not precluded, for example by an inelastic portion of the device body.

In embodiments, the elastic portion 54 of the body 52 is formed from a material that permits the formation of microchannels 62, or micropathways, between the inner surface of the elastic portion 54 and the restraining plug 56 when hydrostatic pressure builds up in the drug reservoir 60. As described in detail herein, the micropathways may extend along the surface of the restraining plug/elastic portion from the drug reservoir to either an unsealed distal opening of the device body, as shown in FIGS. 1-3, or a preformed release port adjacent the restraining plug, as shown in FIGS. 9-10. The elastic portion may include materials that are water-permeable, water-impermeable, or a combination thereof.

In a first aspect, as shown in FIGS. 1A-1D, the drug delivery devices 50 described herein include one or more restraining plugs 56 in contact with the elastic portion(s) 54 of the device body 52, to permit drug release via the distal opening(s) of the device body, as described in U.S. Patent Application Publication 2016/0008271 to Lee, which is incorporated by reference herein in relevant part. However, in contrast to the no-orifice (i.e., no predefined aperture system) of U.S. Patent Application Publication 2016/0008271 to Lee, in certain embodiments, as shown in FIGS. 2 and 3A, the devices include at least one preformed through-hole (i.e., orifice) 66 disposed in a wall of the device body 52.

Thus, in certain embodiments, as shown in FIGS. 1-4, a drug delivery device 50 includes a body 52 that has a wall bounding a reservoir 60 defined within the body 52, the wall having at least one preformed through-hole 66 disposed therein and including a water-permeable portion 64, the body 52 including an elastic portion 54; a drug formulation 58 which contains a drug, the drug formulation 58 being disposed within the reservoir 60; and at least one restraining plug 56 closing off an opening of the body 52 and contacting the elastic portion 54 of the body 52, the opening being in fluid communication with the reservoir 60. The water-permeable portion 64 of the wall is configured to permit water to enter the drug delivery device 50 and contact the drug formulation 58 located in the reservoir 60 and release of the drug 58 from the device 50 is controlled by at least one of (i) release of the drug 58 through the at least one preformed through-hole 66 (i.e., aperture, orifice) in the wall, and (ii) release of the drug through the transient formation of one or more microchannels 62 between the elastic portion 54 of the body 52 and the at least one restraining plug 56, extending to the opening, upon the generation of a hydrostatic pressure effective to form the one or more microchannels 62. In these embodiments, the restraining plugs 56 may be partially or wholly unsealed at the distal end openings of the device 50. Such systems have been found to provide consistent and reproducible drug release profiles, while providing a relief valve system that beneficially provides release of the drug when the through-hole is partially or fully clogged. Thus, the device may operate to release drug via the preformed orifice unless and until the hydrostatic pressure within the drug reservoir reaches a threshold pressure of the restraining plug(s), at which point release via the restraining plugs occurs. For example, release of the drug through the at least one preformed through-hole may be osmotically driven.

Beneficially, this device design provides drug release at the side and/or center of the device, which provides increased device design flexibility as well as potential manufacturability improvements as compared to devices in which the release of the drug occurs only through the distal openings of the device.

In a second aspect, as shown in FIGS. 9-10, the drug delivery devices 50 described herein include sealed distal ends (shown sealed with adhesive 70), with one or more restraining plugs 56 in contact with the elastic portion(s) 54 of the device body 52, to permit drug release via preformed release port(s) 68 in the device body 52 (e.g., sidewall) adjacent the restraining plug 56. The elastic portions 54 may be at or near the ends of the device 50 (as shown in FIGS. 9-10), or may be otherwise disposed along the length of the device, such as at or near the center of the device. The retraining plug(s) 56 may be situated adjacent the one or more preformed release port(s) 68 in the device body 52, such that the restraining plug(s) 56 cover, and effectively close, the preformed release port(s) 68 when the threshold hydrostatic pressure within the drug reservoir 60 has not been reached. In such embodiments, the restraining plugs 56 and elastic portions 54 of the device may be similar to those described above and in U.S. Patent Application Publication 2016/0008271 to Lee, except that the one or more microchannels 62 transiently formed upon the drug reservoir 60 reaching a threshold hydrostatic pressure extend from the drug reservoir 60 to the preformed release port(s) 68.

Thus, in certain embodiments, as shown in FIGS. 9-10, a drug delivery device 50 includes a tubular body 52 that comprises a wall bounding a reservoir 60 defined within the body, the wall having a water-permeable portion 64 and an elastic portion 54 having at least one preformed release port 68 (e.g., through-hole, aperture, orifice, slit) disposed therein; a drug formulation 58 which contains a drug, the drug formulation 58 being disposed within the reservoir 60, wherein the water-permeable portion 64 of the wall permits water to enter the drug delivery device and contact the drug formulation 58 located in the reservoir 60; and at least one restraining plug 56 secured within the reservoir 60 in contact with the elastic portion 54 of the body 52 and adjacent the at least one preformed release port 68, such that the at least one restraining plug 56 controls release of the drug from the device, via the at least one preformed release port 68, by the transient formation of one or more microchannels 62 between the elastic portion 54 of the body and the at least one restraining plug 56, extending to the at least one preformed release port 68, upon the generation of a hydrostatic pressure within the reservoir 60 effective to form the one or more microchannels 62. In certain of these embodiments, the at least one preformed release port 68 is a through-hole or a slit disposed in the wall of the body 52.

Figure 9B:
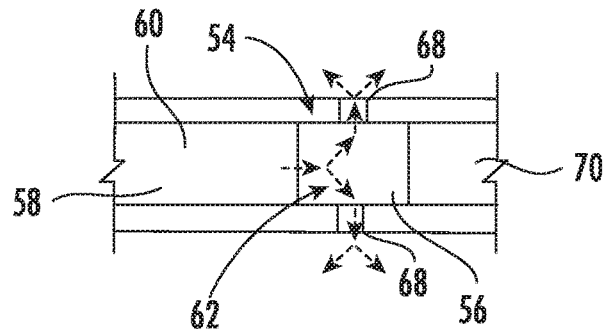
FIG. 9B is an enlarged cross-sectional view of the device of FIG. 9A.
Figure 10B:
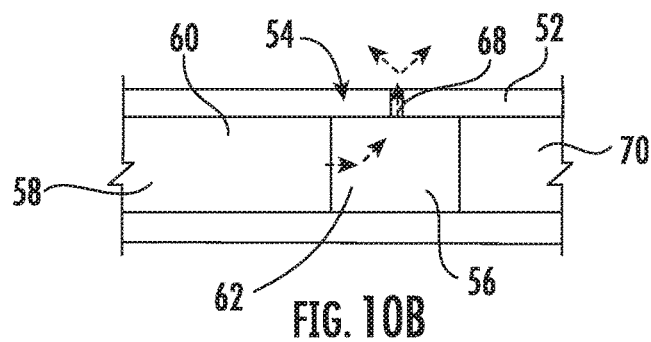
FIG. 10B is an enlarged cross-sectional view of the device of FIG. 10A.

Any suitable number and location of restraining plugs 56 and preformed release ports 68 may be used, to achieve the desired drug release profile. For example, as shown in FIG. 9B, the device 50 may include two preformed ports 68, here shown as apertures, spaced 180 degrees from one another in a tubular device body 52, such that a single restraining plug 56 is positioned adjacent both apertures. As shown in FIG. 9B, a pair of apertures 68 and a corresponding restraining plug 56 may be provided at or near each distal end of the device. For example, as shown in FIG. 10B, a single preformed port 68, here shown as a slit, may be disposed adjacent each restraining plug 56. As shown in FIG. 10B, a preformed port 68 and a corresponding restraining plug 56 may be provided at or near each distal end of the device.

In such embodiments, a suitable adhesive 70, or other sealing means described herein, may be used to seal the ends of the device body. In certain embodiments, the restraining plug 56 is sealed in place via the adhesive 70 or other sealing means sealing the end(s) of the device body, or via another adhesive. Such device designs may reduce complexity and variability associated with manufacturing and assembly of the beveled end plug used when release is from the at least partially unsealed end opening of the device. Further, such release ports allow for the creation of check valves on the side and/or at the middle of the device, allowing drug release from any location along the device, which decreases the limitations of the design. Additionally, locating release of the drug away from the ends of the device beneficially allows for a rounded (i.e., non-trimmed) device end, such as a sphere or ball-shaped end design, which reduces imperfections that may serve as nucleation points for encrustation, at the ends. Further, such device designs advantageously allow for increasing the flexibility and bendability of the terminal ends of the device.

In certain embodiments, the device also includes at least one preformed through-hole disposed in the wall of the body, as described above, in combination with the preformed release port adjacent a restraining plug, such that release of the drug from the device is further controlled by release of the drug through the at least one preformed through-hole in the wall.

In embodiments in which the drug formulation is solid or semi-solid, as described in further detail below, the device may be configured to permit, in vivo, water to diffuse through the water-permeable portion of the wall and into the reservoir to solubilize the drug formulation.

The devices described herein have been discovered to advantageously provide controlled release of drug via these improved one-way valve release mechanisms, alone or in combination with other release mechanisms such as preformed sidewall orifices, which may experience clogging. Thus, the devices described herein provide for a longer duration of drug delivery as compared to devices with sidewall release orifices alone, which may be susceptible to encrustation.

Specifically, controlled release of drug can be achieved with the transient formation of microchannels through which a fluidized drug can be dispensed from a delivery device, either through the distal end opening of the device or through one or more preformed release ports adjacent a restraining plug. The microchannels form at an interface of device components in response to a hydrostatic pressure developed in a drug reservoir, such that the device parameters can be tailored to release drug only when a certain threshold hydrostatic pressure is reached within the drug reservoir.

To facilitate the formation of microchannels, the elastic portion 54 of the device body 52 and the restraining plugs 56 may be formed from materials having a certain elasticity or hardness. In embodiments, the Shore durometer of the elastic portion of the body is lower than the Shore durometer of the restraining plug. In one embodiment, the Shore durometer of the elastic portion of the body is from about 40 A to about 60 A, and the Shore durometer of the restraining plug is from about 70 A to about 100 A. In another embodiment, the Shore durometer of the elastic portion of the body is from about 45 A to about 55 A, and the Shore durometer of the restraining plug is from about 75 A to about 85 A. In a further embodiment, the Shore durometer of the elastic portion of the body is about 50 A, and the Shore durometer of the restraining plug is about 80 A. In yet another embodiment, the Shore durometer of the elastic portion of the body is from about 40 A to about 60 A, and the Shore durometer of the restraining plug is about 97 A. In some embodiments, in which the restraining plug is at or near the end of the device and a preformed release port in the device body is adjacent the restraining plug, the durometer of the restraining plug may be further reduced to decrease the rigidity of the end of the device.

In embodiments, the device body 52 may contain two or more elastic portions 54 having different elasticities that contact two or more restraining plug 56 having different elasticities. This configuration can be useful for controlling drug release from two or more different reservoirs having drugs of different solubilities, desired release rates, etc. For example, a water-permeable body may have a first and a second elastic portion made from two different materials having Shore durometers of 45A and 55A, respectively, and inserted into the first and the second elastic portion may be a first and a second restraining plug made from two different materials having Shore durometers of 75A and 85A, respectively.

In one embodiment, the device body is made entirely from an elastic material. In other embodiments, the body is made from at least one elastic material and at least one inelastic material. In further embodiments, the body is made from a material having at least one elastic portion and at least one inelastic portion.

The elastic portion 54 of the device body 52 may be any shape that permits the insertion of a restraining plug 56 and the creation of interference fit between the elastic portion 54 and the plug 56. When viewed in cross-section, the lumen of the elastic portion may be non-polygonal. For example, the cross-section may be round, substantially round, or oval-shaped. In some embodiments, the shape of the lumen of the elastic portion substantially conforms to the shape of the restraining plug.

The device body 52 generally may be made from any biocompatible material, so long as at least a portion of the body 64 is water-permeable. The elastic portion 54 of the body 52 that contacts the restraining plug 56 may be made from any biocompatible material that permits the formation of one or more microchannels 62 through which drug may exit the device 50.

In one embodiment, the device body 52 includes an elongated tube. An interior of the tube may define one or more drug reservoirs 60, and a drug formulation 58 may be housed in the drug reservoir(s) 60. For example, the elongated tube may be annular in shape with the annulus, i.e., the lumen of the tube, serving as the drug reservoir. In other embodiments, the drug reservoir portion is in a form other than a tube. The release rate of the drug from the drug reservoir portion generally is controlled by the design of the combination of the device components, including but not limited to the materials, dimensions, surface area, preformed release ports/through-holes, and restraining plugs, as well as the particular drug formulation and total mass of drug load, among others.

An example of the drug reservoir portion 78, i.e., a device body, is shown in FIG. 4. As shown, the drug reservoir portion 78 may include a body formed from an elastomeric tube 82. The tube 82 defines a reservoir 60 that contains a number of drug units 158. Into the openings in the ends of the tube 82, restraining plugs are inserted.

In embodiments, the drug reservoir portion 78 and drug reservoir 60 operate as an osmotic pump. In such embodiments, the drug reservoir portion is formed, at least in part, from a water-permeable material. In a preferred embodiment, the water-permeable material is silicone. Following insertion/implantation into a patient's body, water or urine permeates through a wall of the drug reservoir portion. The water enters the reservoir, contacts the drug formulation, forming a fluidized drug (e.g., a drug solution) which can then be dispensed at a controlled rate out of the reservoir through microchannels that form between the restraining plugs and the elastic portion of the drug reservoir portion. The delivery rate and overall performance of the osmotic pump is affected by device parameters, such as the surface area of the drug reservoir portion; the permeability to liquid of the material used to form the drug reservoir portion; the relative dimensions, shapes, and positions of the preformed release ports/through-holes in the device body; the relative dimensions, shapes, and elasticity or hardness of the restraining plugs and the elastic portion of the drug reservoir lumen; and the drug formulation dissolution profile, among other factors. In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Application Publication 2009/0149833 to Cima et al.

The drug reservoir portion may be formed, at least in part, from an elastomeric material, which may permit elastically deforming the device for its insertion into a patient, e.g., during its deployment through deployment instrument such as a cystoscope or catheter. For example, the tube may be elastically deformed along with the retention frame for intravesical insertion, as described in further detail below.

In one embodiment, the drug reservoir portion is formed from a material that is both elastomeric and water-permeable. Examples of materials that are both elastomeric and water-permeable include silicones and thermoplastic polyurethanes known in the art. Other suitable biocompatible materials, including inelastic biocompatible materials, also may be used.

The length, diameter, and thickness of the drug reservoir portion may be selected based on the volume of drug formulation to be contained, the desired rate of delivery of the drug, the intended site of deployment of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of medical grade silicone tubing, as known in the art. Other suitable non-resorbable materials may be used. In other embodiments, the device body is at least partially bioerodible. In one embodiment of a bioerodible device, the drug reservoir portion is formed of a biodegradable or bioresorbable polymer. Any suitable biocompatible polymers may be used.

In embodiments in which the drug reservoir portion is tube-shaped, the drug reservoir portion tube may be substantially linear and, in some cases, may be substantially cylindrical with a circular or oval cross-section, although square, triangle, hexagon, and other polygonal cross-sectional shapes can be used, among others.

In one embodiment, the drug reservoir portion 78 has multiple reservoirs. Each reservoir may be defined by a portion of the drug reservoir inner surface and at least one partition. In embodiments in which the drug reservoir portion is tube-shaped, the partition may be a partition structure or plug inserted into the tube, such as a cylinder, sphere, or disk, among others, in which case the partition structure may have a larger cross-section than the tube, securing the partition structure in place and segregating adjacent reservoirs. The partition may be non-porous or semi-porous, non-resorbable or resorbable and may be formed of a material described herein with reference to the restraining plugs. The partition also may be formed in the tube, such as by molding. For example, one or more webs may extend through the tube along its length to segregate axial reservoirs that extend along the length of the tube. The partition also may be a structure that joins two different tubes that serve as separate reservoirs.

The multiple reservoirs permit segregating two or more different drug formulations in different reservoirs, delivering a single drug from different reservoirs at different rates or times following deployment, or combinations thereof. For example, two different reservoirs may be in communication with two different restraining plugs having different configurations, as described herein, which permit the drugs in the two different reservoirs to be released at different rates. The two different reservoirs also may house the same or different drug formulations in the same or different forms (such as liquid, semi-solid, and solid), or combinations thereof. Coatings or sheaths also may be provided along different portions of a single drug reservoir or along different drug reservoirs housing the same or different drug formulations. The coatings or sheaths may be used to alter the water-permeability of the water-permeable body. These embodiments can be combined and varied to achieve the desired release profile of the desired drug.

For example, the onset of release of two doses in different reservoirs can be staged by configuring the device accordingly, such as by using different materials (e.g., materials with different water-permeabilities) for portions of the tube defining different reservoirs, by placing drugs with different solubilities in the reservoirs, or by placing drugs with different forms in the reservoirs, such as a liquid form for immediate release and a solid form to be solubilized in vivo prior to release. Thus, the device may release some drug relatively quickly after deployment while other drug may experience an induction time before beginning release.

Preformed Release Apertures/Ports

In some embodiments, the device includes one or more ports (e.g., apertures, orifices, slits, and the like) for dispensing the drug, such as via generation of an osmotic pressure within the drug reservoir, as described herein. The apertures may be spaced along the tube to provide a passageway for release of the drug formulation. The apertures or orifices may be positioned through a sidewall of the tube. The apertures may be in fluid communication with one or more reservoirs (as illustrated by orifice 66 in FIGS. 2 and 3A) or may be adjacent a restraining plug (as illustrated by ports 68 in FIGS. 9 and 10), as described herein.

An embodiment of an aperture 66 is shown on the drug reservoir portion 78 in FIG. 3A. The aperture 66 may be located about a middle of the drug reservoir portion 78 or adjacent to an end of the drug reservoir 60, which may affect the ease of loading solid drug units 158 into the drug reservoir portion 78 as described below. The apertures may be positioned away from a portion of the tube that will be folded during insertion to limit tearing of degradable membranes on the apertures.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 500 μm, such as between about 25 μm and about 300 μm, and more particularly between about 30 μm and about 200 μm. In one particular example, the aperture has a diameter between about 100 μm and about 200 μm, such as about 150 μm. In one particular example, the aperture has a diameter between about 25 μm and about 100 μm, such as about 75 μm. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube.

In some embodiments, as shown in FIG. 10, the preformed release port 68 is a slit in the device body 52, which is configured to provide an outlet for the drug 58 upon generation of a pressure sufficient to stretch the elastic portion 54 of the body 52 in which the port 68 is formed to open the slit and thereby provide a through-hole for the drug solution. Such a slit may be configured to function as a one-way valve, permitting release out from the device when opened by internal pressure and otherwise remaining closed so that external fluids do not pass into the device.

Restraining Plugs

The restraining plugs 56 may have any shape suitable for placement in the one or more elastic portions 54 of the body 52 that permits the formation of microchannels 62 as described herein. In embodiments, the restraining plugs 56 are cylindrical or substantially cylindrical. As used herein, the term "substantially cylindrical" refers to any shape that is non-polygonal when viewed in cross-section. In other embodiments, the restraining plugs are partially cylindrical or substantially cylindrical, and have at least one portion that is wedged, tapered, angled, or rounded. In embodiments, the restraining plugs are solid, not hollow.

Figure 5:
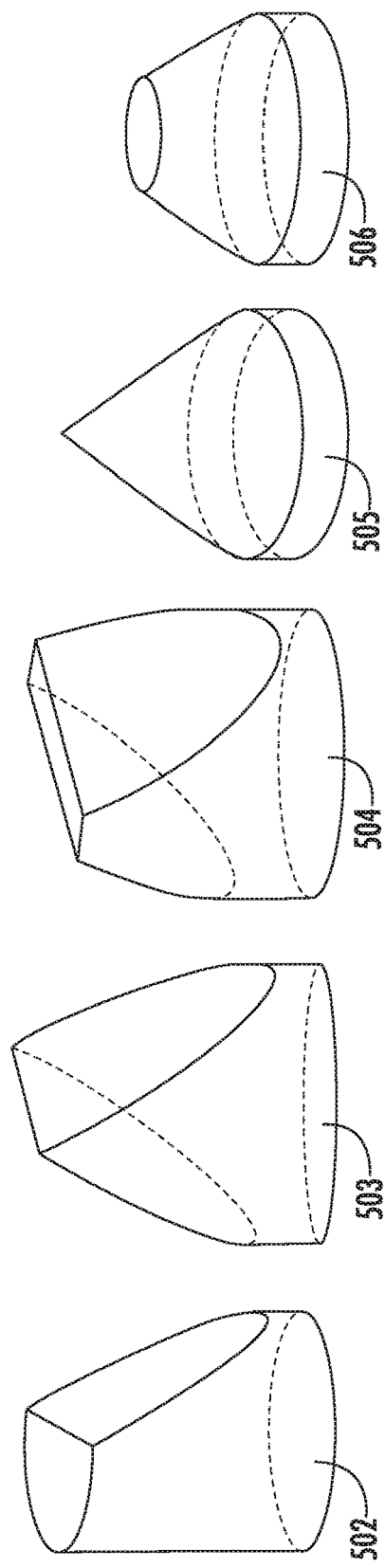
FIG. 5 illustrates various embodiments of restraining plugs in accordance with the present disclosure.
Figure 6:
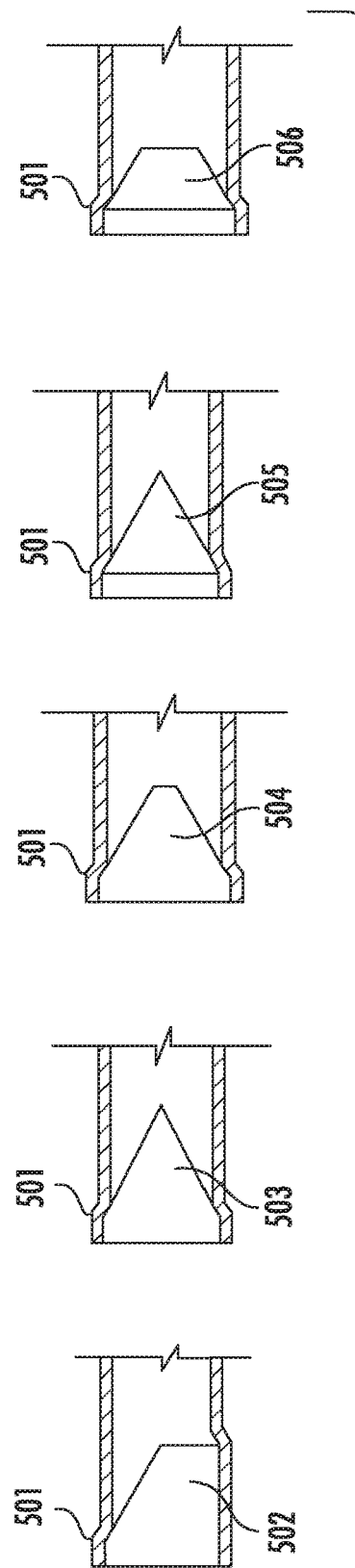
FIG. 6 is a cross-sectional view illustrating the restraining plugs of FIG. 5 in use as the end plugs of a drug delivery device.

FIG. 5 depicts a series of restraining plugs 502, 503, 504, 505, and 506 having different shapes. FIG. 6 depicts the restraining plugs 502, 503, 504, 505, and 506 inserted into a tubeshaped elastic portion 501 of a device body. When the restraining plug has a wedged, tapered, angled, or rounded surface, these surfaces may allow the microchannels described herein to form more easily. Not wishing to be bound by any particular theory, it is believed that the wedged, tapered, angled, or rounded surfaces may provide a preferential path for osmotic flow along or near such surfaces. As a result, less hydrostatic pressure may be required to create one or more microchannels between the restraining plug and the elastic portion of the water-permeable body. Generally, the restraining plugs may have one or more wedged, tapered, angled, or rounded surfaces on one side or both sides of the restraining plugs' longitudinal axis. In embodiments, the angle between the longitudinal surface of the restraining plug and the surface of the wedged, tapered, angled, or rounded portion may be from about 30° to about 60°.

As shown in FIG. 6, the wedged, tapered, angled, or rounded surfaces of the restraining plugs 502, 503, 504, 505, 506 can be inserted into the end of the tube-shaped elastic portion 501 so that the wedged, tapered, angled, or rounded surfaces of the restraining plugs are in communication with the interior (drug reservoir) of the drug delivery devices. In FIG. 6, the opposed base of the restraining plugs faces outward, as an exterior surface of the drug delivery devices. Alternatively, in other embodiments, the position may be reversed, so that the wedged, tapered, angled, or rounded surfaces of the restraining plug face outward, as an exterior surface of the drug delivery devices, while the base of the restraining plug is in communication with the interior (drug reservoir) of the drug delivery devices. In this position, the wedged, tapered, angled, or rounded surfaces of the restraining plugs may create a void space at or near the end of the elastic portion. The void space or a portion thereof may host an adhesive, clamp, plug, or other known means for securing the restraining plug, as illustrated in FIGS. 3A-3C.

In certain embodiments, the elastic portion of the body and the restraining plug may be disposed at a location of the device other than at the terminal end.

The restraining plugs 56 should contact the elastic portions 54 of the water-permeable body 52 in a manner that prohibits the restraining plug 56 from being expelled from the elastic portion 54 when the device 50 is compressed in the body after deployment and/or when a hydrostatic force is exerted on the restraining plug 56. In embodiments, the restraining plug 56 and the elastic portion 54 are secured together by an interference fit, e.g., by frictional engagement, with one another, alone or optionally with the aid of an adhesive. The restraining plug 56 should remain in the elastic portion 54 of the water-permeable body 52 when the device 50 is elastically deformed between its retention shape and relatively straightened shape.

In a preferred embodiment, the restraining plugs 56 do not migrate within the elastic portions 54 of the device body 52 after deployment and during drug release. In other embodiments, the restraining plugs 56 do migrate within the elastic portions 54 of the water-permeable body 52 after deployment and during drug release. Migration of the restraining plugs 56 can be tolerated as long as the drug release is not undesirably affected.

In embodiments, the cross-sectional shape of the restraining plugs 56 substantially conforms to the inner dimensions of the elastic portion 54 of the device body 52. In other embodiments, the outer diameter of the restraining plugs 56 exceeds the inner diameter of the elastic portion 54 of the device body 52. The phrase "inner diameter," as used herein, is not intended to imply that the elastic portion is always circular when viewed in cross-section; instead, the term refers to the largest diameter or major axis of the lumen of the elastic portion of the water-permeable body. Similarly, the phrase "outer diameter," as used herein, is not intended to imply that the restraining plug, when viewed in cross-section, is always circular; instead, the term refers to the largest diameter or major axis of the cross-section of the restraining plug or its base.

In one embodiment, the outer diameter of the restraining plug exceeds the inner diameter of the elastic portion of the device body by at least 3 percent. In another embodiment, the outer diameter of the restraining plug exceeds the inner diameter of the elastic portion of the device body by at least 5 percent. In yet another embodiment, the outer diameter of the restraining plug exceeds the inner diameter of the elastic portion of the device body by at least 10 percent. In a further embodiment, the outer diameter of the restraining plug exceeds the inner diameter of the elastic portion of the device body by at least 15 percent. In a still further embodiment, the outer diameter of the restraining plug exceeds the inner diameter of the elastic portion of the device body by at least 20 percent. In a particular embodiment, the outer diameter of the restraining plug exceeds the inner diameter of the elastic portion of the body by at least 25 percent.

In one embodiment, the outer diameter of the restraining plug exceeds the inner diameter of the elastic portion of the device body by about 5 percent, and the inner diameter of the elastic portion of the device body is between 2.1 and 2.2 mm, (e.g., 2.16 mm) and the outer diameter of the restraining plug is between 2.2 and 2.3 mm (e.g., 2.27 mm). The restraining plug, in this embodiment, has a length of from about 2.5 mm to about 5 mm.

In another embodiment, the outer diameter of the restraining plug exceeds the inner diameter of the elastic portion of the water-permeable body by about 28 percent. For example, in one case, the inner diameter of the elastic portion of the water-permeable body is between 2.1 and 2.2 mm (e.g., 2.16 mm), and the outer diameter of the restraining plug is between 2.7 and 2.8 mm (e.g., 2.77 mm). The restraining plug, in this embodiment, has a length of from about 2.5 mm or 5 mm long.

The restraining plugs may be of any length that is suited for allowing the formation of microchannels between the restraining plug and the elastic portion of the device body. The outer surface of the restraining plug may contact the inner surface of the elastic portion of the device body along the entire length of the restraining plug or for only a portion of the restraining plug's length. For example, the outer surface of a restraining plug shaped like a cylinder may contact the inner surface of the opening in the elastic portion of the water-permeable body along the entire length of the restraining plug. The outer surface of a restraining plug having one or more wedged, angled, or tapered surfaces, however, may only contact the inner surface of the elastic portion of the water-permeable body along a portion of the restraining plug's overall length, as shown, for example, in FIGS. 3 and 6.

In embodiments, the length of the restraining plug may be from about 2 mm to about 10 mm, from about 2 mm to about 8 mm, from about 2 to about 6 mm, or from about 2.5 mm to about 5 mm.

Generally, the inner surface of the elastic portion of the water-permeable body and the restraining plug may be shaped so that the restraining plug and the elastic portion of the water-permeable body remain in contact with each other during deployment. In some embodiments, as shown in FIG. 3, adhesive 70 may be used to secure together the elastic portion 54 of the water-permeable body 52 and the restraining plug 56. A single portion or one or more discrete portions of adhesive may be used as long as the amount and placement of adhesive does not undesirably impact the drug release as described herein. In other embodiments, the restraining plug may be secured mechanically. For example, an external clamp may be used to secure together the elastic portion of the water-permeable body and the restraining plug. Any suitable clamp may be used as long as it does not undesirably impact tolerability of the device to the patient or the drug release as described herein. When the restraining plug is secured mechanically, with adhesive, or both, it may be necessary to form the elastic portion or the restraining plug or both with a softer material to ensure the formation of microchannels.

The restraining plugs may be made from any biocompatible material or combination of biocompatible materials that permits the release of drug from the device as described herein. For example, the restraining plugs may be made from a polymer, such as silicone or ethylene vinyl acetate, a ceramic, an adhesive, or a combination thereof.

In certain embodiments, the restraining plugs are coated with a material to inhibit undesired bonding between the inner surface of the elastic portion and the restraining plug, such as may occur with certain polymeric materials when the assembled device is sterilized, e.g., by gamma irradiation. For example, the restraining plugs may be silicone and coated with parylene, such as parylene C.

The Retention Frame Portion

In a preferred embodiment, as shown in FIGS. 3 and 4, the drug delivery device 50 includes a retention frame portion 76. The retention frame portion 76 is associated with the drug reservoir portion 78 and permits retaining the drug reservoir portion 78 in the body, such as in the bladder. The retention frame portion 76 may include a retention frame 74 that is deformable between a relatively expanded shape and a relatively lower-profile shape. For example, the retention frame 74 may naturally assume the relatively expanded shape, may be manipulated into the relatively lower-profile shape for insertion into the body, and may spontaneously return to the relatively expanded shape upon insertion into the body. The retention frame 74 in the relatively expanded shape may be shaped for retention in a body cavity, and the retention frame 74 in the relatively lower-profile shape may be shaped for insertion into the body through the working channel of a deployment instrument such as a catheter or cystoscope. To achieve such a result, the retention frame 74 may have an elastic limit, modulus, and/or spring constant selected to impede the device from assuming the relatively lower-profile shape once deployed. Such a configuration may limit or prevent accidental expulsion of the device from the body under expected forces. For example, the device may be retained in the bladder during urination or contraction of the detrusor muscle.

In a preferred embodiment, the retention frame 74 includes or consists of an elastic wire. For example, in the embodiment shown in FIGS. 3 and 4, the retention frame 74 is an elastic wire formed from a superelastic alloy, such as nitinol, and surrounded by the wall 84 of the retention frame lumen 80, which forms a protective sheath about the retention frame 74. The wall 84 may be formed from a polymer material, such as silicone. In some other embodiments, the retention frame may be an elastic wire formed from a superelastic alloy, such as nitinol, that is covered in a polymer coating such as a silicone sheath and is attached to the drug reservoir portion. In still other embodiments, the elastic wire may be formed of a relatively low modulus elastomer.

In some embodiments, the retention frame lumen 80 may include the retention frame 74 and a filling material, such as a polymer filling. An example filling material is a silicone adhesive, such as MED3-4213 by Nusil Technology LLC, although other filling materials may be used. The filling material may completely or partially fill the void in the retention frame lumen 80 about the retention frame 74. For example, the filling material may be poured into the retention frame lumen 80 about the retention frame 74 and may cure therein. The filling material may reduce the tendency of the drug reservoir lumen 60 to stretch along, or twist or rotate about, the retention frame 74, while maintaining the drug reservoir lumen 60 in a selected orientation with reference to the retention frame 74. The filling material is not necessary, however, and may be omitted.

When the retention frame 74 is in the relatively expanded shape, such as the coiled shape shown in FIG. 3A, the device 50 may occupy a space having dimensions suited to impede expulsion from the bladder. When the retention frame is in the relatively lower-profile shape, such as the elongated shape shown in FIG. 7, the device 700 may occupy a space suited for insertion into the body, such as through the working channel of a deployment instrument 702. The properties of the elastic wire cause the device to function as a spring, deforming in response to a compressive load but spontaneously returning to its initial shape once the load is removed.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provides a spring constant without which the frame would significantly deform under the forces of urination. For example, the retention frame may include one or more windings, coils, spirals, or combinations thereof, specifically designed to achieve a desirable spring constant as described in U.S. Application Publication 2009/0149833 to Cima et al.

The retention frame may have a two-dimensional structure that is substantially confined to a plane, a three-dimensional structure, such as a structure that occupies the interior of a spheroid, or some combination thereof.

Drug Formulations

The term "drug" as used herein encompasses any suitable pharmaceutically active ingredient. The drug may be small molecule, macromolecule, biologic, or metabolite, among other forms/types of active ingredients. The drug described herein includes its alternative forms, such as salt forms, free acid forms, free base forms, and hydrates. The drug may be formulated with one or more pharmaceutically acceptable excipients known in the art. Non-limiting examples of the drug include gemcitabine, oxaliplatin, and/or another chemotherapeutic agent; trospium and/or another antimuscarinic agent; and/or lidocaine and/or another anesthetic agent. In one embodiment, the first compartment may be loaded with two or more types of drug tablets (e.g., different drugs), so that a combination of drugs may be delivered.

In embodiments, the drug is one used to treat pain. A variety of anesthetic agents, analgesic agents, and combinations thereof may be used. In one embodiment, the drug is an anesthetic agent. The anesthetic agent may be a cocaine analogue. The anesthetic agent may be an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocalne, ropivacaine, and trimecaine. Representative examples of aminoesters or ester-class anesthetics include amylocalne, benzocaine, butacaine, chloroprocaine, cocaine, cyclomethycaine, dimethocaine, hexylcaine, larocaine, mepryl-caine, metabutoxycaine, orthocaine, piperocaine, procaine, proparacaine, propoxycaine, proxymetacaine, risocaine, and tetracaine. The drug also can be an antimuscarinic compound that exhibits an anesthetic effect, such as oxybutynin or propiverine. In embodiments, the analgesic agent includes an opioid. Representative examples of opioid agonists include alfentanil, allylprodine, alphaprodine, anileridine, benzyl morphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, di methylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated. Representative examples of other suitable pain relieving agents include such agents as salicyl alcohol, phenazopyridine hydrochloride, acetaminophen, acetylsalicylic acid, flufenisal, ibuprofen, indoprofen; indomethacin, naproxen.

In certain embodiments, the drug is one used to treat inflammatory conditions such as interstitial cystitis, radiation cystitis, painful bladder syndrome, prostatitis, urethritis, post-surgical pain, and kidney stones. Non-limiting examples of drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin.

In certain embodiments, the drug is one used to treat urinary incontinence, frequency, or urgency, including urge incontinence and neurogenic incontinence, as well as trigonitis. Drugs that may be used include anticholinergic agents, antispasmodic agents, anti-muscarinic agents, □-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutylin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), Z D-6169 (Zeneca Co., United Kingdom), and stilonium iodide.

In certain embodiments, the drug is one used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include *Bacillus* Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an anti-leukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). Other intravesical cancer treatments include small molecules, such as Apaziquone, adriamycin, AD-32, doxorubicin, docetaxel, epirubicin, gemcitabine, HTI-286 (hemiasterlin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In certain embodiments, the drug is one used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In certain embodiments, the drug is one used to treat fibrosis of a genitourinary site, such as the bladder or uterus. Representative examples of drugs for the treatment of fibroids include pentoxphylline (xanthine analogue), anti-TNF, antiTGF agents, GnRH analogues, exogenous progestins, antiprogestins, selective estrogen receptor modulators, danazol and NSAIDs.

In certain embodiments, the drug is one used to treat neurogenic bladder. Representative examples of such drugs include analgesics or anaesthetics, such as lidocaine, bupivacaine, mepivacaine, prilocalne, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including GABAB agonists such as baclofen; botulinum toxins; capsaicins; α-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., Spinal Cord 42:267-72 (2004).

In certain embodiments, the drug is one used to treat incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include α-adrenergic agonists, estrogens, β-adrenergic agonists, tricyclic antidepressants (imipramine, amitriptyline). In still another embodiment, the drug is selected from those known for facilitating bladder emptying (e.g., α-adrenergic antagonists (phentolamitie) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., M3 muscarinic agonist, choline ester).

In some embodiments, an agent that increases the osmotic pressure may be disposed in the water-permeable body or included in the drug formulation or, in some embodiments, the drug itself may act as an osmotic agent. For example, the drug and osmotic agent can be homogeneously mixed or compressed into tablets. As another example, a drug tablet may be disposed near a restraining plug, and an osmotic agent can be arranged next to the drug tablet. Non-limiting examples of osmotic agents include urea, citric acid, L-tartaric acid, lactose-fructose, dextrose-fructose, sucrose-fructose, mannitol-fructose, sodium chloride, fructose, lactose-sucrose, potassium chloride, lactose-dextrose, mannitol-dextrose, dextrose-sucrose, mannitol-sucrose, sucrose, mannitol-lactose, dextrose, potassium sulfate, mannitol, sodium phosphate tribase.12H$_2$O, sodium phosphate dibasic.7H$_2$O, sodium phosphate dibasic anhydrous, and sodium phosphate monobasic.H$_2$O.

Use and Applications of the Device

The device may be deployed in a body cavity or lumen, and subsequently may release one or more drugs for the treatment of one or more conditions, locally to one or more tissues at the deployment site and/or regionally to other tissues distal from the deployment site. The release may be controlled over an extended period. Thereafter, the device may be removed, resorbed, excreted, or some combination thereof.

In one example, the device is inserted into the body by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 7, which shows the device 700 assuming a retention shape as the device exits a deployment instrument 702. The deployment instrument 702 may be any suitable lumen device, such as a catheter, urethral catheter, or cystoscope. The deployment instrument 702 may be a commercially available device or a device specially adapted for the present drug delivery devices, for example, as described in U.S. Patent Application Publication 2011/0202036 to Boyko et al.

Once inserted into the body, the device releases the drug in a controlled manner. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. In a preferred embodiment, the device is an intravesical drug delivery device, which releases a therapeutic amount of a drug continuously into urine in the bladder over a selected treatment period ranging from 7 days to 60 days, e.g., from 14 days to 30 days. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug exits the device via the microchannels described herein. For example, the drug may be solubilized upon contact with urine in cases in which the device is deployed in the bladder.

Subsequently, the device may be retrieved from the body, such as in cases in which the device is non-resorbable, non-collapsible, or otherwise needs to be removed.

The device also may be configured to be completely or partially bioresorbable, such that retrieval is unnecessary. In one case, the device is resorbed or sufficiently degraded that it can be expelled from the bladder during urination. In some embodiments, the device include biodegradable links such that the device can collapse into a shape that permits passage through the urethra during urination, as described in U.S. Pat. No. 8,690,840 to Lee et al., which is incorporated herein by reference. The device may not be retrieved or resorbed until some of the drug, or preferably most or the entire drug, has been released.

Figure 8:
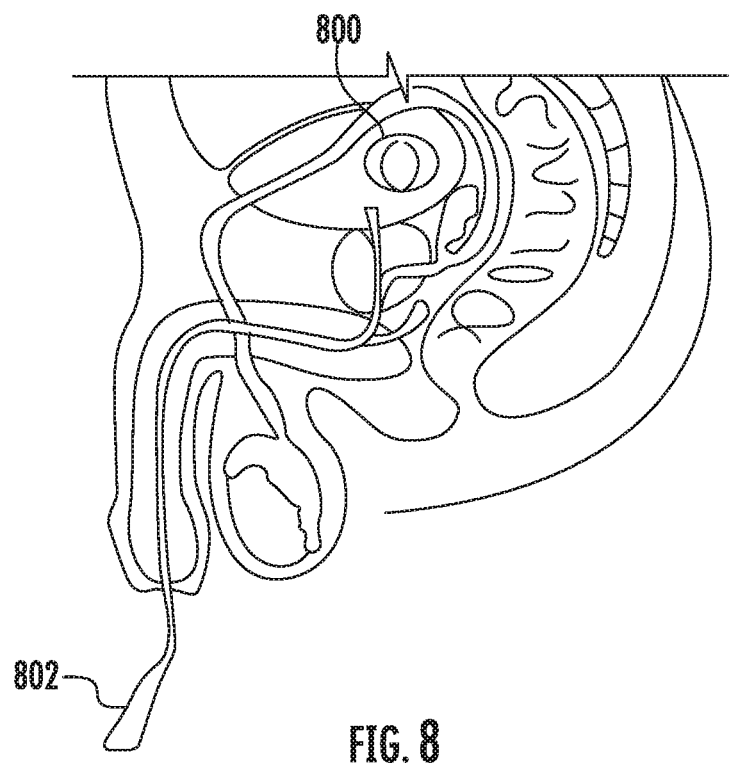
FIG. 8 illustrates deployment of a drug delivery device in a patient.

FIG. 8 illustrates the deployment of a device 800 into the bladder, wherein the adult human male anatomy is shown by way of example. A deployment instrument 802 may be inserted through the urethra to the bladder, and the device 800 may be passed through the deployment instrument 802, driven by a stylet and/or a flow of lubricant or other fluid, for example, until the device 800 exits into the bladder. Thus, the device is deployed into the bladder of a male or female human patient in need of treatment.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the drug delivery device, with a self-contained drug payload, is deployed wholly within the bladder to provide sustained delivery of at least one drug to the bladder in an amount that is therapeutically effective for the target tissue in need of treatment. It may be the bladder itself or regionally proximate to the bladder. Such regional delivery may provide an alternative to systemic administration, which may entail undesirable side effects or result in insufficient bioavailability of the drug. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In one embodiment, the intravesical drug delivery device is deployed into a bladder to locally deliver lidocaine or another anesthetic agent for management of pain arising from any source, such as a disease or disorder in genitourinary tissues, or pain stemming from any bladder procedure, such as surgery, catheterization, ablation, medical device implantation, or stone or foreign object removal, among others.

In embodiments, the drug delivery device is sterilized, such as after the device is manufactured/assembled and before the device is deployed into the patient. In some cases, the device may be sterilized after the device is packaged, such as by subjecting the package to gamma irradiation, electron beam irradiation, or ethylene oxide gas. Although gamma irradiation may affect the performance of certain aspects of the drug delivery devices, materials and configurations can be chosen, as explained herein, to eliminate or substantially neutralize any adverse effects.

In one aspect, a method of administering a drug to a patient includes inserting any of the drug delivery devices described herein into a lumen or body cavity of a patient; and permitting water influx into the reservoir to develop a pressure in the reservoir effective to cause the drug to flow from the reservoir through any preformed through-holes present in the device body and through one or more microchannels formed between the restraining plug and the elastic portion of the device body from (i) the drug reservoir and at least one preformed release port or (ii) the drug reservoir and an opening at the end of the device, and out of the device and into the lumen or body cavity. In certain embodiments, the body cavity is the bladder of the patient.

In some particular embodiments, trospium is locally administered into the bladder of a patient for the treatment of neurogenic detrusor overactivity (NDO) resulting from a spinal cord injury (SCI). In some embodiments, the patient is one who has been diagnosed to have traumatic or non-traumatic suprasacral SCI for longer than 6 months and a documented history of NDO. Such a patient may also need to use an intravesical catheter (non-indwelling) to empty his or her bladder. In some of these embodiments, the local administration of the trospium into the urinary bladder of the patient is accomplished using one of the drug delivery systems described herein. In some particular embodiments, the device (containing a payload of trospium, e.g., tablets comprising trospium chloride) is placed into the bladder through an inserter and then the device is removed 30 to 60 days later, such as 42 days later. The device releases the trospium gradually, continuously, during the indwelling time. In some of these embodiments, the device releases trospium at a daily average rate of from about 2 mg/day to about 30 mg/day, for example from about 5 mg/day to about 25 mg/day, such as from about 5 mg/day to about 15 mg/day, or about 10 mg/day, over the treatment period, e.g., over a 42-day indwelling time. In some other embodiments, the trospium may be locally administered into the urinary bladder by other delivery systems known in the art, for example as described in U.S. Patent Application Publication No. 2015/0182516 to Giesing, which is incorporated herein by reference.

In some particular embodiments, trospium is locally administered into the bladder of a patient for the treatment of idiopathic overactive bladder (iOAB) and urinary incontinence. In some embodiments, the patient is one who has been diagnosed to have symptoms of OAB (frequency/urgency) with urge urinary incontinence or mixed urinary incontinence with a predominant urge component for at least 6 months. In some of these embodiments, the local administration of the trospium into the urinary bladder of the patient is accomplished using one of the drug delivery systems described herein. In some particular embodiments, the device (containing a payload of trospium, e.g., tablets comprising trospium chloride) is placed into the bladder through an inserter and then the device is removed 30 to 60 days later, such as 42 days later. The device releases the trospium gradually, continuously, during the indwelling time. In some of these embodiments, the device releases trospium at a daily average rate of from about 2 mg/day to about 30 mg/day, for example from about 5 mg/day to about 25 mg/day, such as from about 5 mg/day to about 15 mg/day, or about 10 mg/day, over the treatment period, e.g., over a 42-day indwelling time. In some other embodiments, the trospium may be locally administered into the urinary bladder by other delivery systems known in the art, for example as described in U.S. Patent Application Publication No. 2015/0182516 to Giesing, which is incorporated herein by reference.

The present invention may be further understood with reference to the following non-limiting examples.

Example 1

Prototypes of devices having a central laser-drilled orifice were manufactured and loaded with trospium chloride tablets. One set of the devices included two spacer orifices (i.e., plugs having longitudinal orifices formed therein) at each end, with the second set of devices having two restraining plugs at the ends. Illustrations of the prototypes are shown at FIGS. 11 and 12. The device of FIG. 11 has three drug release apertures: two at the opposing ends and one in the sidewall. The device had a drug reservoir lumen inner diameter of 2.64 mm and a wall thickness of 0.2 mm. The wall had a durometer of 50 A. The device of FIG. 12 has one release aperture plus two opposing ends capable of providing release upon sufficient osmotic pressure to form microchannels. The device had a drug reservoir lumen inner diameter of 2.64 mm and a wall thickness of 0.2 mm. The wall had a durometer of 50 A.

The devices were placed in containers of deionized water and the amount of trospium chloride released over time was measured. Results of in vitro tests (five for each prototype design) are shown in the graphs of FIGS. 11 and 12. As can be seen, the restraining plugs achieve a consistent, reproducible release profile, as compared to the less reproducible release profile of the spacer orifice device. The observed difference between the two systems was not predictable.

Example 2

The device illustrated in FIG. 3 was manufactured as follows. The device was a dual lumen silicone tube with a laser-machined orifice, parylene C coated silicone elastomer plugs to contain the drug as well as to form one-way valve at each end of the drug compartment in the drug lumen, and white silicone adhesive in the large lumen to hold the plugs in place, a pre-formed superelastic nitinol wireform housed in the retention frame lumen, and retention lumen ends sealed with translucent silicone adhesive. The drug was formed as tablets containing trospium chloride (pharmaceutical active ingredient), povidone (polyvinylpyrrolidone (PVP)) K29/32 (a binding agent excipient), and polyethylene glycol 8000 (a lubricant excipient). Each device contained 850 mg of trospium chloride. The device is small in size (less than 5 cm on the long axis), flexible, and contoured, in order to minimize potential irritation and inflammation. The drug reservoir lumen had an inner diameter of 2.64 mm and a wall thickness of 0.41 mm. The nitinol wire had a thickness of 0.279 mm.

The device body serves as an osmotic pump and provides passive controlled release of the drug when filled with drug while the nitinol wireform provides bladder retention of the system during a treatment period while the system remains free-moving in the bladder. The device, as an osmotic pump, delivers the therapeutic agent at a controlled rate by osmosis. The silicone tube wall housing the trospium mini-tablets acts as a semipermeable membrane, and the thickness of the wall can modulate water flux into the system and eventually control the drug release rate. There are multiple drug release channels in the system; one in the middle of the system, and the others are at the ends. The rate of drug delivery is controlled by water permeability of a semipermeable membrane and the osmotic properties of therapeutic and osmotic agent in the lumen. Trospium chloride has a high water solubility and is its own osmotic agent; no additional osmotic agent is included. This particular device was designed to deliver trospium chloride at a rate of approximately 10 mg/day.

Figure 13:
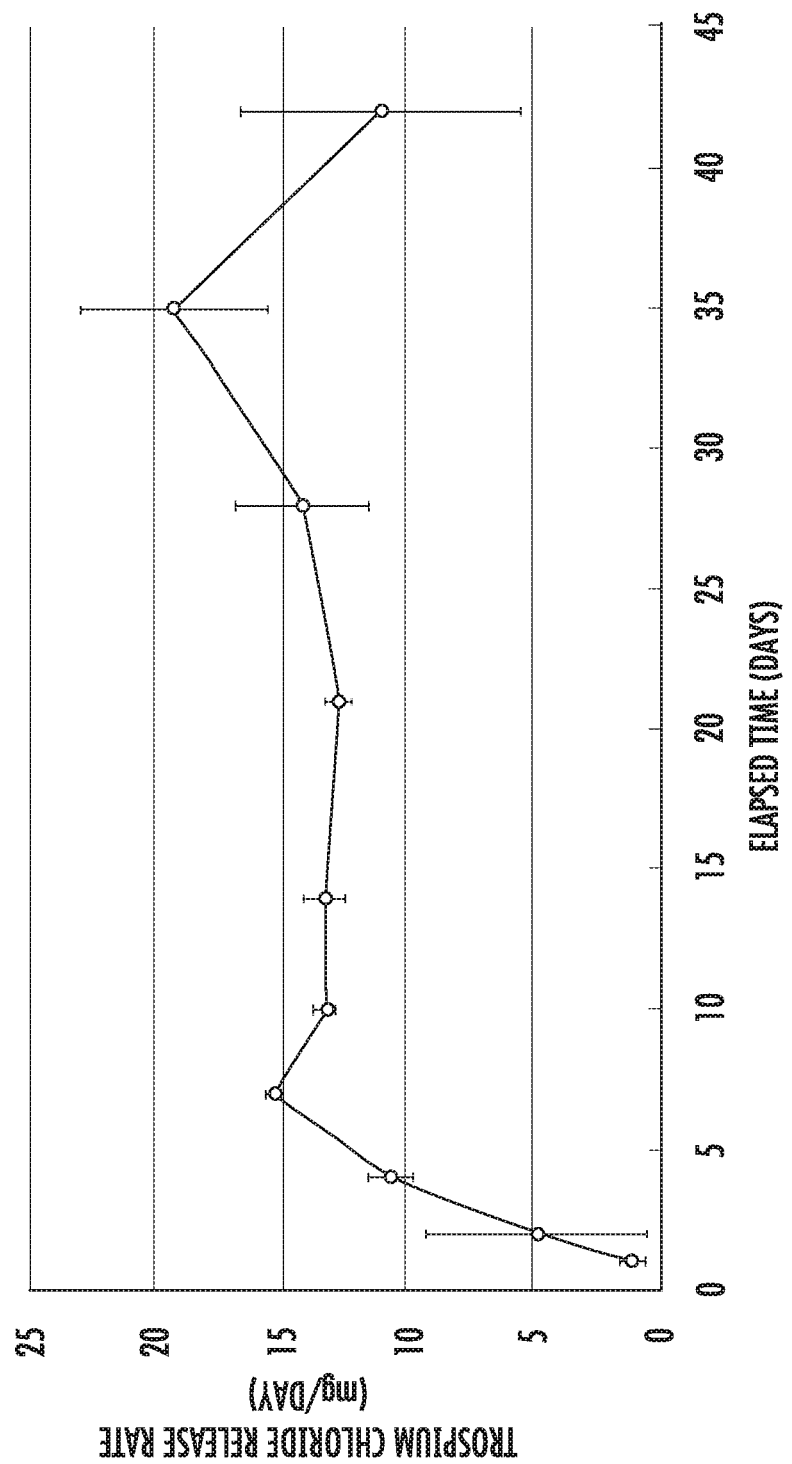
FIG. 13 is a graph showing drug release rate over time for a drug delivery device tested in the Examples.

The system was placed in deionized water at 37° C., and the rate of release of the trospium was determined. The in vitro results (average±SD, n=3) are shown in FIG. 13. As can be seen, the average daily release rate was approximately 10 mg/mL. Thus, it was determined that the system can be tailored to provide a desired daily release profile of trospium chloride.

Example 3

Trospium releasing intravesical devices were manufactured for in vitro release characterization, according to the parameters of Table 1. The devices were manufactured using one of two types of silicone housing parts. One type (RW) included an annular tube having a wall thickness of 0.2 mm bounding the drug reservoir lumen and having a 50 A durometer. The other type (TW) included an annular tube having a wall thickness of 0.4 mm bounding the drug reservoir lumen and having a 35 A durometer. Both of the types of silicone parts had a drug reservoir lumen inner diameter of 2.64 mm. All of the devices had a 150 μm diameter laser-drilled orifice, which was approximately centered in the sidewall of the silicone part. Systems were assembled using plugs of different lengths. Systems either contained two plugs, one on each end, or one plug with a spacer on the other end of the system that seals that end of the reservoir (i.e., such that no microchannels can form at that end). The drug reservoir lumen of each system was filled with approximately 996 mg of trospium chloride tablets, with a composition of 95 percent trospium chloride-polyvinylpyrrolidone (PVP) granules with a 97:3 ratio (percent w/w), and 5 percent polyglycol 8000 PF (PEG 8 k) by mass. Trospium chloride acted as both the active agent and osmotic agent to drive the osmotic drug release mechanism. A total of 42 device systems were used for this in vitro stability characterization. All systems were irradiated.

For the RW systems, first-order trospium release kinetics was observed after initial peak release rates of approximately 18 to 24 mg/day by day 7. The TW systems had an initial peak release rate between 10 and 15 mg/day with constant release rates of 10 to 14 mg/day over the next 35 days. The RW systems displayed a higher cumulative release than the TW systems, but the number of plugs present in the systems and the length of the plugs had no effect on the release rates of the systems.

TABLE 1

Device information

| System No. | Tablet Mass (mg)* | Drug Core Length (cm)** | Type of Silicone Body Part | Plug Length (mm) | Plug No. | Spacer No. |
|---|---|---|---|---|---|---|
| 1 | 1000.6 | 15.6 | RW | 5 | 1 | 1 |
| 2 | 993.5 | 15.6 | | | | |
| 3 | 1003.3 | 15.5 | | | | |
| 4 | 999.8 | 15.7 | | | 2 | 0 |
| 5 | 998.3 | 15.8 | | | | |
| 6 | 989.9 | 15.5 | | | | |
| 7 | 990.9 | 15.6 | | 8 | 1 | 1 |
| 8 | 994.5 | 15.4 | | | | |
| 9 | 995.3 | 15.6 | | | | |
| 10 | 993.2 | 15.5 | | | 2 | 0 |
| 11 | 999.8 | 15.5 | | | | |
| 12 | 992.9 | 15.5 | | | | |
| 13 | 992.7 | 15.5 | | 16 | 1 | 1 |
| 14 | 991.1 | 15.4 | | | | |
| 15 | 993.9 | 15.6 | | | | |
| 16 | 996.8 | 15.7 | | | 2 | 0 |
| 17 | 991.3 | 15.6 | | | | |
| 18 | 986.6 | 15.7 | | | | |
| 19 | 992 | 15.4 | TW | 5 | 1 | 1 |
| 20 | 994.5 | 15.3 | | | | |

TABLE 1-continued

Device information

| System No. | Tablet Mass (mg)* | Drug Core Length (cm)** | Type of Silicone Body Part | Plug Length (mm) | Plug No. | Spacer No. |
|---|---|---|---|---|---|---|
| 21 | 1000.6 | 15.4 | | | | |
| 22 | 997.6 | 15.5 | | | 2 | 0 |
| 23 | 990.5 | 15.3 | | | | |
| 24 | 1000.8 | 15.5 | | | | |
| 25 | 990.9 | 15.4 | | 8 | 1 | 1 |
| 26 | 1001.3 | 15.4 | | | | |
| 27 | 992.1 | 15.4 | | | | |
| 28 | 1000.9 | 15.6 | | | 2 | 0 |
| 29 | 1002.8 | 15.6 | | | | |
| 30 | 1002.2 | 15.7 | | | | |
| 31 | 997.8 | 15.3 | | 16 | 1 | 1 |
| 32 | 994.9 | 15.5 | | | | |
| 33 | 1000.7 | 15.5 | | | | |
| 34 | 996.7 | 15.6 | | | 2 | 0 |
| 35 | 998.9 | 15.5 | | | | |
| 36 | 992.2 | 15.5 | | | | |
| 37 | — | 15 | RW | 8 | 2 | 0 |
| 38 | — | 15 | | | | |
| 39 | — | 15 | | | | |
| 40 | — | 15 | TW | | | |
| 41 | — | 15.1 | | | | |
| 42 | — | 15.1 | | | | |

*The total linear length of the tablets was approximately 14.9 cm when the tablets were serially laid out
**Approximate linear length between two spacer surfaces facing the tablets when the system was straightened All irradiated units were used for in vitro release testing. Each unit was placed in a glass jar filled with 300.00+/−0.05 g degassed deionized water and put in an environmental chamber kept at 37° C. Samples were taken from each jar at predetermined time points (T=1, 2, 4, 7, 10, 14, 21, 28, 35, and 42 days). At each time point, release jars were inverted 15 times and a 1 mL sample was taken and replaced with 1 mL fresh release media. At days 14 and 28, the release media was fully replaced. Trospium time point samples were analyzed using high-performance liquid chromatography (HPLC) operated by MassLynx.

Figure 22:
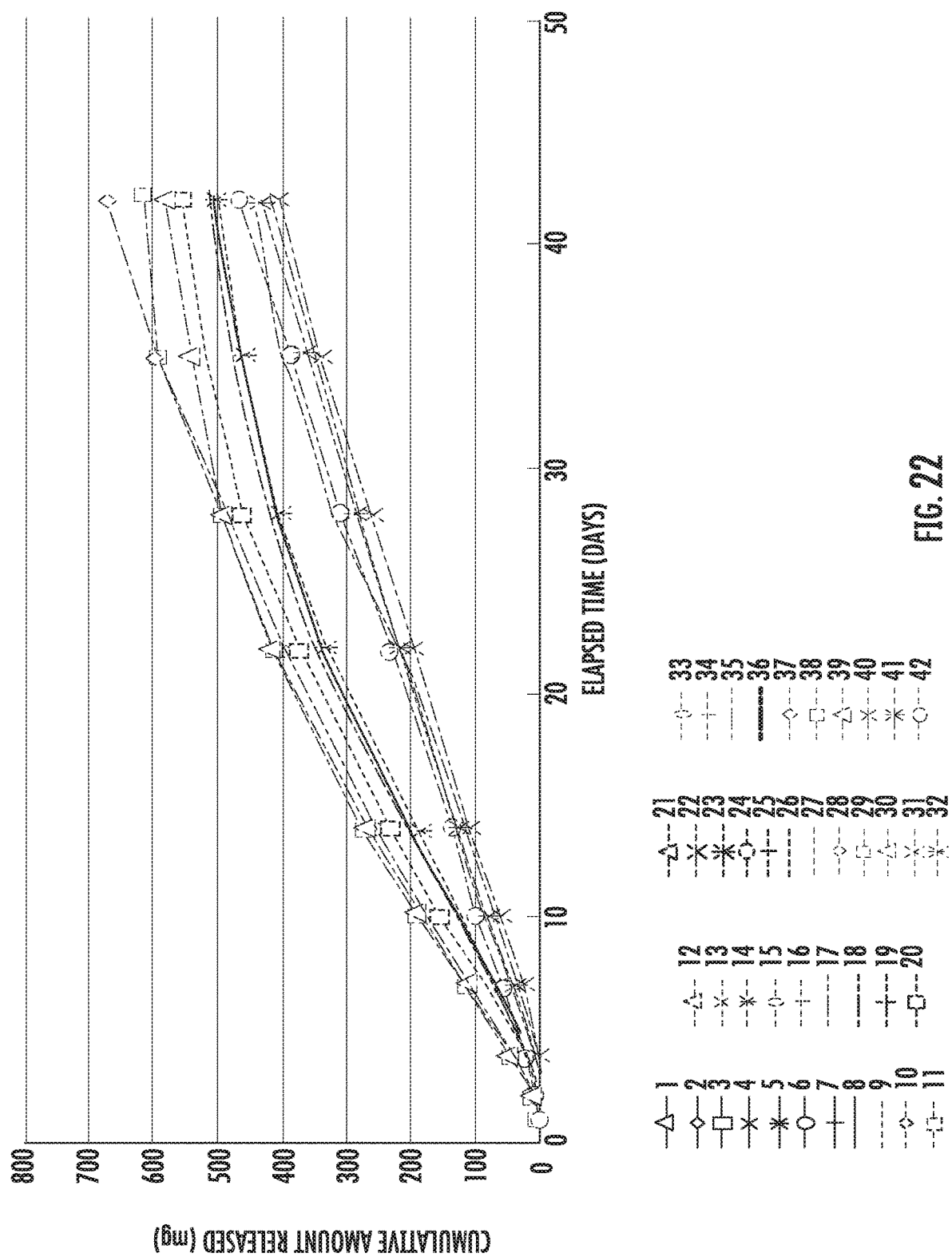
FIG. 22 is a graph showing cumulative drug release over time for various drug delivery devices tested in the Examples.
Figure 23:
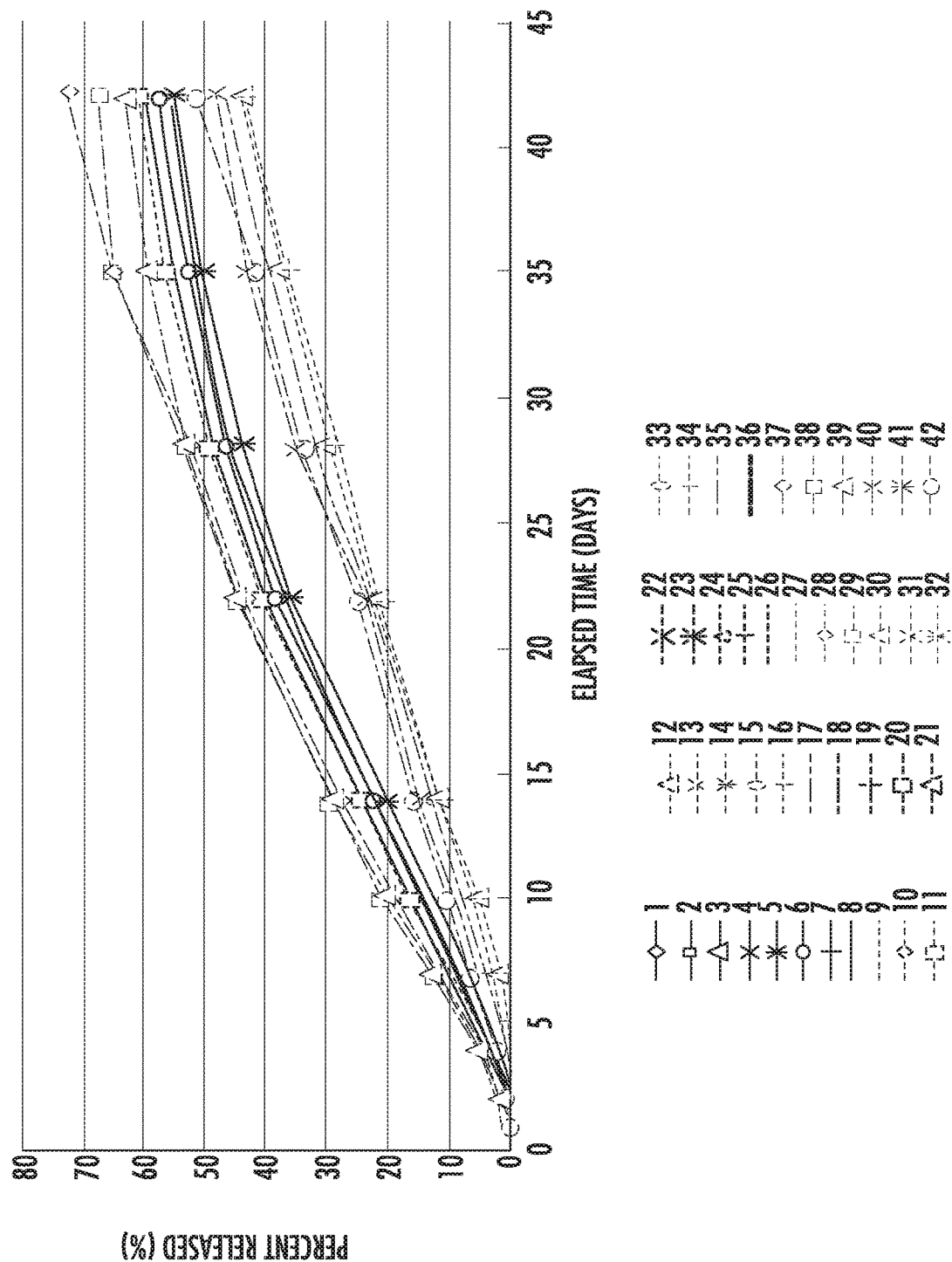
FIG. 23 is a graph showing percent drug release over time for various drug delivery devices tested in the Examples.

Trospium chloride release rate (mg/day) at a given time point T(i) was estimated using a backward difference method according to Equation 1:

$$\text{Release rate at } T(i) \text{ (mg } FBE/\text{day}) = \frac{M(i) - M(i-1)}{T(i) - T(i-1)} \quad \text{(Eq. 1)}$$

where M(i) and M(i−1) are cumulative amount released at the current time point T(i) and the previous time point T(i−1), respectively. The cumulative amount of trospium released data seen in FIG. 22 was used to create the trospium chloride rate of release profiles seen in FIGS. 18 through 21. The initial drug load was used to estimate the percent amount of trospium released which can be seen in FIG. 23. The average cumulative percent of trospium released for each configuration type can be seen in Table 2 below.

TABLE 2

Average percent released at days 4, 21, and 42 for each device configuration

| System Characteristics | | | | | Average cumulative Percent Released (%) | | | | | |
|---|---|---|---|---|---|---|---|---|---|---|
| | | Plug | | | Day 4 | | Day 21 | | Day 42 | |
| Tubing Type | Plug/Spacer configuration | Length (mm) | n | Media Type | Avg | RSD(%) | Avg | RSD(%) | Avg | RSD(%) |
| RW 50A | 1 plug and 1 spacer | 5 | 3 | DI Water | 1.64 | 33.45 | 38.76 | 2.81 | 57.19 | 4.88 |
| | 2 plugs | 5 | | | 2.36 | 8.28 | 38.31 | 2.62 | 57.33 | 2.43 |
| | 1 plug and 1 spacer | 8 | | | 0.54 | 124.04 | 37.42 | 3.70 | 56.62 | 2.82 |
| | 2 plug | 8 | | | 2.41 | 8.68 | 38.56 | 4.83 | 58.31 | 4.76 |
| | 1 plug and 1 spacer | 16 | | | 1.29 | 34.07 | 37.29 | 2.76 | 56.17 | 1.44 |
| | 2 plugs | 16 | | | 1.20 | 55.14 | 37.54 | 1.77 | 55.75 | 0.94 |
| TW 35A | 1 plug and 1 spacer | 5 | | | 0.59 | 38.33 | 23.77 | 5.97 | 45.81 | 2.95 |
| | 2 plugs | 5 | | | 1.09 | 15.34 | 24.28 | 1.30 | 46.43 | 0.77 |
| | 1 plug and 1 spacer | 8 | | | 0.58 | 31.10 | 24.55 | 2.03 | 46.71 | 2.57 |
| | 2 plugs | 8 | | | 0.93 | 36.62 | 23.68 | 4.07 | 45.62 | 1.26 |
| | 1 plug and 1 spacer | 16 | | | 0.48 | 49.24 | 23.52 | 5.14 | 45.24 | 3.46 |
| | 2 plugs | 16 | | | 0.58 | 45.41 | 22.75 | 5.11 | 45.15 | 2.86 |
| RW 50A | 2 plugs | 8 | | | 4.92 | 11.95 | 44.77 | 1.32 | 68.10 | 6.76 |
| TW 35A | 2 plugs | 8 | | | 2.02 | 15.43 | 24.82 | 0.52 | 49.24 | 4.25 |

Figure 18:
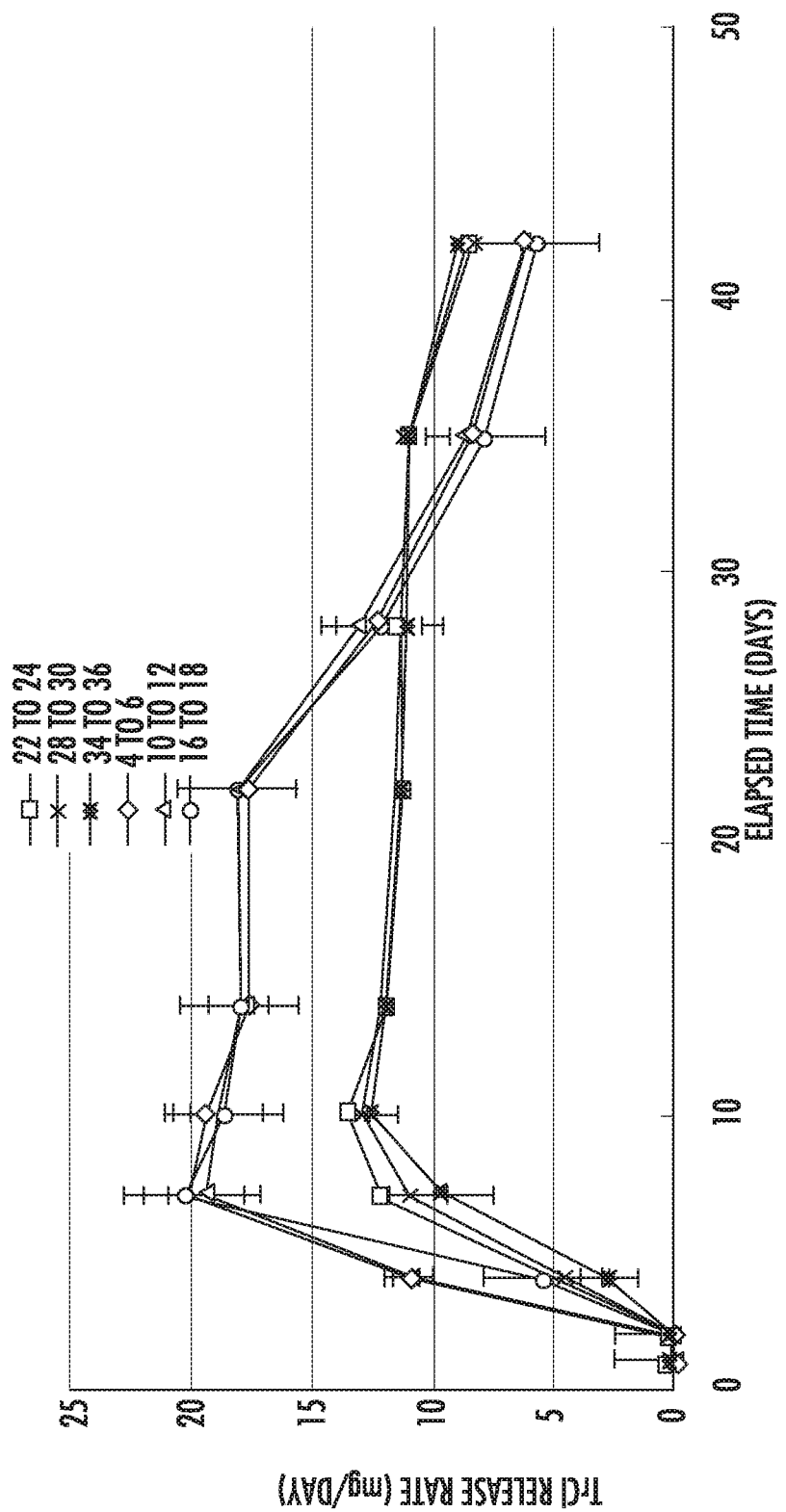
FIG. 18 is a graph showing drug release rate over time for various drug delivery devices tested in the Examples.

RW and TW Systems with Two Plugs (See FIG. 18).

First-order trospium release kinetics were observed after an initial release rate of approximately 18 to 20 mg/day at approximately 7 days since the release experiment started for RW systems with different plug lengths of 5, 8, and 16 mm. After 7 days, a steady decrease in the release rates of the RW systems was observed. At the end of the 42-day experiment, the release rate averaged 5 to 6 mg/day. The initial release rate for TW systems was observed to be approximately 12 to 13 mg/day. After the first 10 days, the release rates remained approximately constant at about 11 to 13 mg/day for the first 35 days. After the first 35 days, first-order trospium release kinetics was observed. At the end of the 42-day experiment, the release rates averaged 8 to 9 mg/day. No change in release rate occurred with a change in plug length. All RW systems with plugs length of 5, 8, or 16 mm displayed the same release profiles, and all TW systems with plugs length of 5, 8, or 16 mm displayed the same release profiles.

Figure 19:
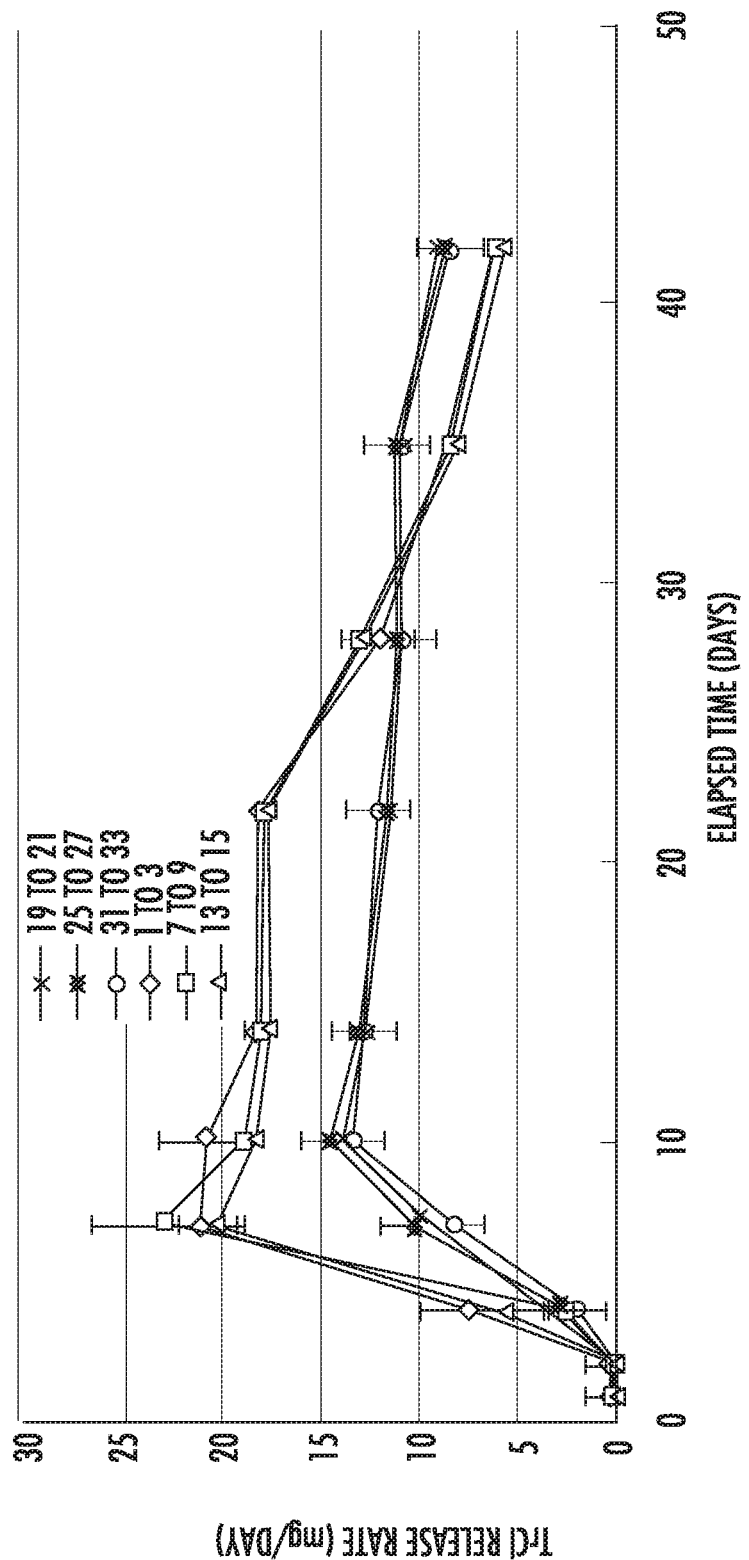
FIG. 19 is a graph showing drug release rate over time for various drug delivery devices tested in the Examples.

System with One Plug and One Spacer (See FIG. 19).

First-order trospium release kinetics were observed after an initial release rate of approximately 20 to 23 mg/day at approximately 7 days since the release experiment started for RW systems with different plug lengths of 5, 8, and 16 mm. After 7 days, a steady decrease in the release rates of the RW systems was observed. At the end of the 42-day experiment, the release rate averaged 5 to 6 mg/day. The initial release rate for TW systems was observed to be approximately 13 to 15 mg/day. After the first 10 days, the release rates remained approximately constant at about 10 to 13 mg/day for the first 35 days. After the first 35 days, first-order trospium release kinetics was observed. At the end of the 42-day experiment, the release rates averaged 8 to 9 mg/day. No change in release rate occurred with a change in plug length. All RW systems with plugs length of 5, 8, or 16 mm displayed the same release profiles, and all TW systems with plugs length of 5, 8, or 16 mm displayed the same release profiles.

Figure 20:
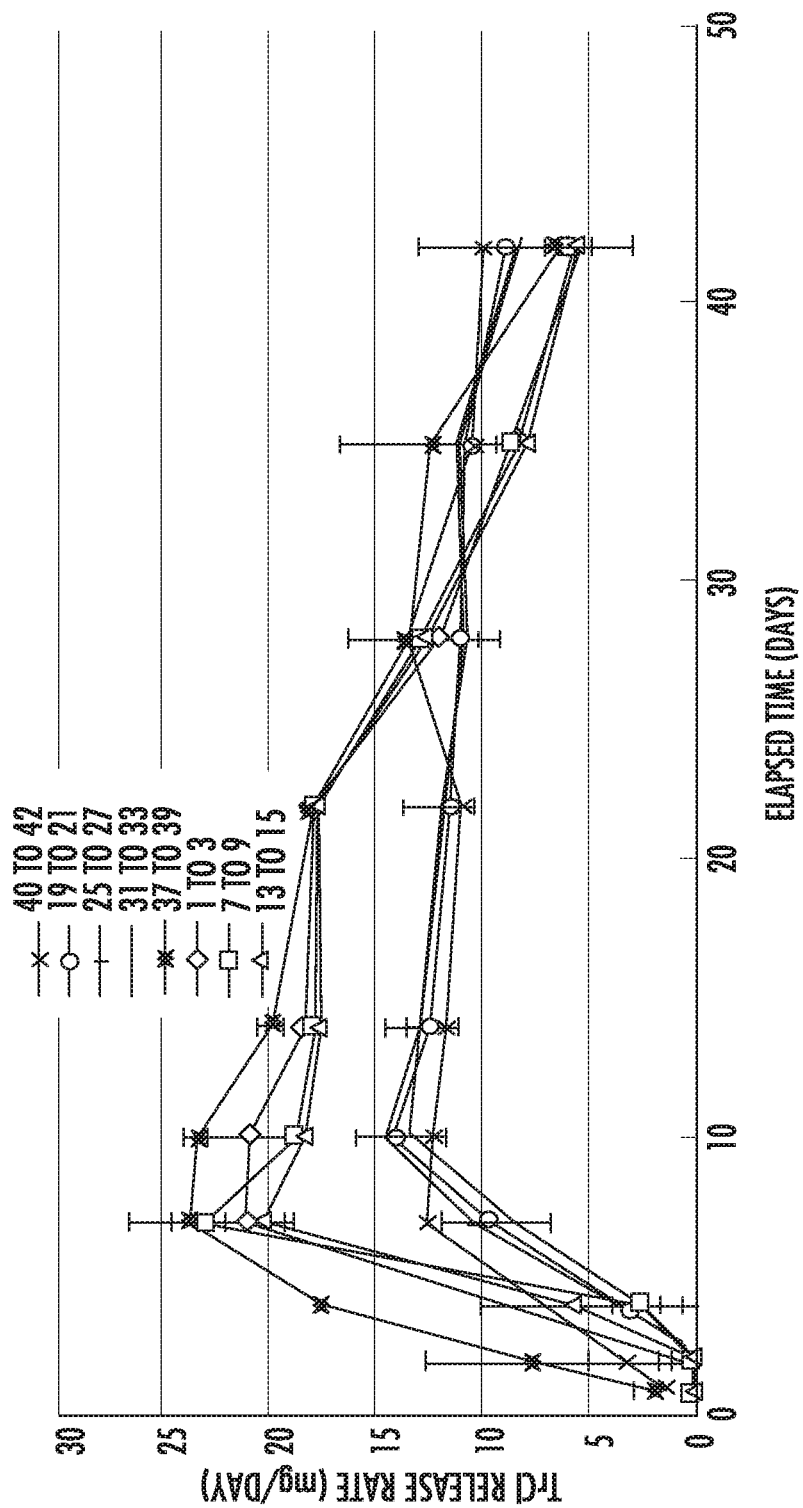
FIG. 20 is a graph showing drug release rate over time for various drug delivery devices tested in the Examples.

System with One Plug and One Spacer as Compared to Two Plug Systems (See FIG. 20).

All RW systems with plugs length of 5, 8, or 16 mm displayed the same release profiles, and all TW systems with plugs length of 5, 8, or 16 mm displayed the same release profiles. Additionally, the RW and TW systems displayed no change in release rate when comparing the one plug systems versus the two plug 8 mm systems from a lot tested in minipigs. Both a change in plug length and the number of plugs present did not change the release rate of the trospium chloride systems.

Figure 21:
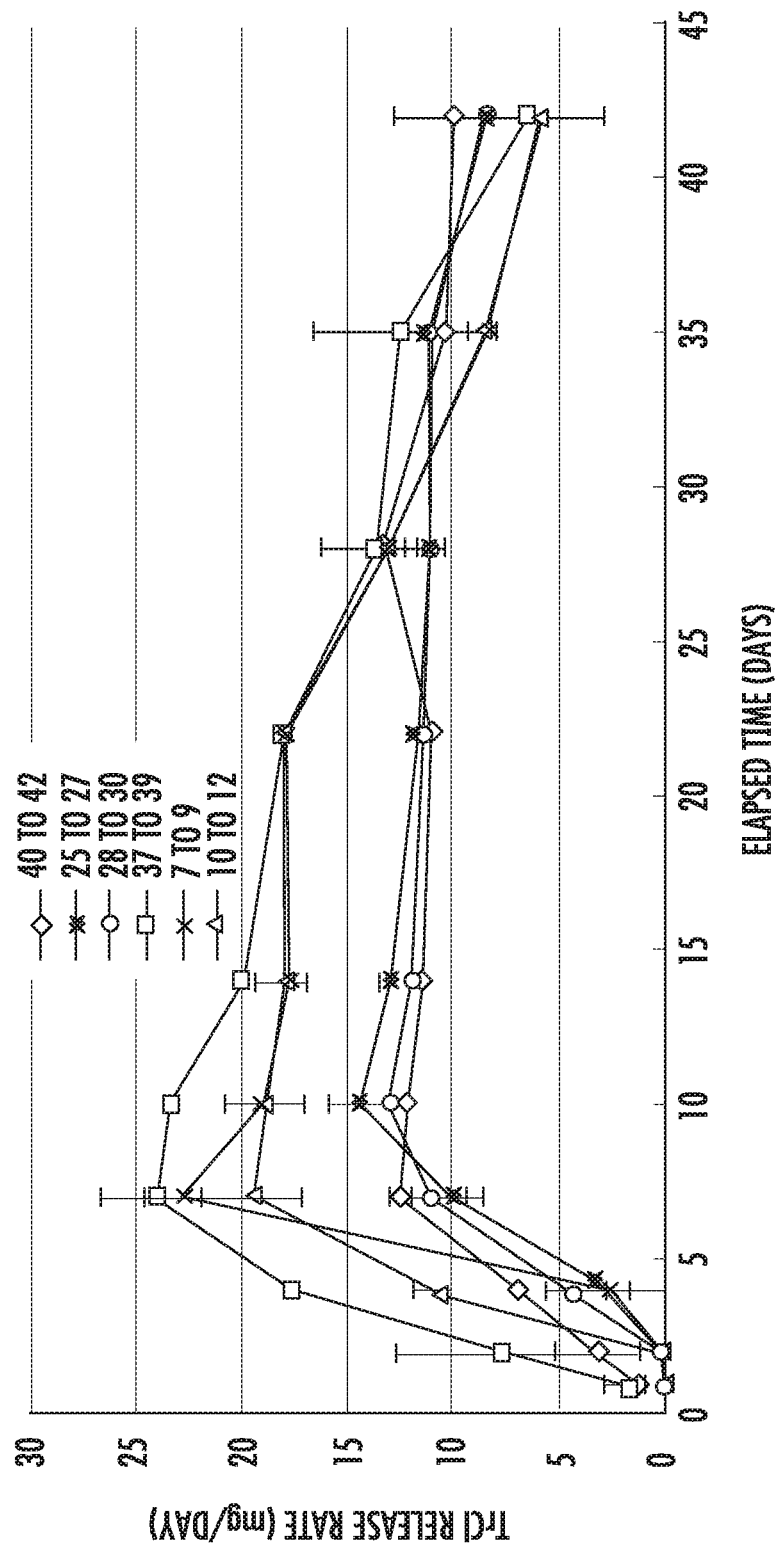
FIG. 21 is a graph showing drug release rate over time for various drug delivery devices tested in the Examples.

Systems with 8 mm Plugs (See FIG. 21).

First-order trospium release kinetics were observed after an initial release rate of approximately 19 to 24 mg/day at approximately 7 days since the release experiment started for RW systems with different plug amounts of 8 mm length. After 7 days, a steady decrease in the release rates of the RW systems was observed. At the end of the 42-day experiment, the release rate averaged 5 to 6 mg/day. The initial release rate for TW systems was observed to be approximately 10 to 13 mg/day. After the first 10 days, the release rates remained approximately constant at about 10 to 14 mg/day for the first 35 days. After the first 35 days, first-order trospium release kinetics was observed. At the end of the 42-day experiment, the release rates averaged 8 to 10 mg/day. No change in release rate occurred with a change in the number of plugs each system contained that were 8 mm in length. All RW systems with plugs length of 8 mm displayed the same release profiles when there was one or two plug in the system, and all TW systems with plugs length of 8 mm displayed the same release profiles when there were one or two plugs in the system.

In conclusion, osmotic trospium releasing devices assembled with 0.2 mm wall thickness (RW) and 0.4 mm wall thickness (TW) loaded with approximately 917 mg of trospium chloride were built and an in vitro release experiment was performed in 37° C. DI water as the release medium. For RW systems, first-order trospium release kinetics were observed after an initial release rate of approximately 18 to 24 mg/day at approximately 7 days after the release experiment started. The initial release rate for the TW systems was approximately 10 to 15 mg/day. For the TW systems, the release rate remained approximately constant at about 10 to 14 mg/day for the first 28 days. After the first 35 days, first-order trospium release kinetics were observed. Therefore, RW systems had a high initial peak release rate and higher cumulative release of the overall drug load by the end of the experiment. TW systems had a more constant release rate for the first 35 days and a lower cumulative release of the overall drug load. There was no change in the release rate profiles with a change in the number of plugs present or the length of the plugs. All the RW systems displayed approximately the same release rate, cumulative release, and percent release. All the TW systems displayed approximately the same release rate, cumulative release, and percent release.

Example 4

Trospium releasing intravesical devices with drug release opening(s) were manufactured for in vitro release testing. Dual lumen silicone tubes were used to construct the systems. The small lumen contained a bi-oval shape wireform and the large lumen was filled with trospium mini-tablets having a composition (percent w/w) of 92 percent trospium chloride, 3 percent PVP, and 5 percent PEG 8K. The amount of trospium chloride loaded in each system was approximately 910 to 920 mg.

Four Punched Hole Configuration.

FIGS. 9A-9B show a configuration where four punched holes are present, two punched holes in the sidewall of the housing near each end of the drug core. The holes were positioned over parylene C coated silicone restraining plugs with a length of 5 mm and outer diameter (OD) of 2.77 mm. Silicone adhesive behind the restraining plugs was used to fix the restraining plugs in place and the adhesive sealed the ends of the lumen. A bi-oval shaped wireform was inserted into the small lumen of the tube, and silicone adhesive was applied into the small lumen to fix the wireform in place and allowed to cure for approximately 24 hours, after which time the ends were trimmed to 5 mm from the end of the restraining plugs. The silicone restraining plugs were oversized; the inner diameter of the silicone tube was 2.64 mm while the outer diameter of the silicone restraining plugs was 2.77 mm. The parylene coating on the restraining plug was used to prevent gamma irradiation induced adhesion at the silicone-to-silicone interface after gamma irradiation was used for product sterilization. The punched holes were placed at 2 to 3 mm from each end of the drug core. The punched holes over the oversized restraining plugs were designed to serve as drug release outlets as osmotic pressure inside the drug chamber is built up.

The location and the number of holes can vary depending on how many and where the restraining plugs are located along the length of the tube. For example, if only one restraining plug and two punched holes are present in the middle of the tube, there will be two drug release openings in the middle of the tube.

Two Slit Opening Configuration.

FIGS. 10A-10B show a configuration where two slits are present in the device, one slit in the sidewall of the housing near each end of the drug core. Parylene C coated silicone restraining plugs with a length of 5 mm and outer diameter of 2.77 mm were inserted into the tube and then the slits were created by razor blade. The razor blade passed through the tube wall and penetrated partially into the restraining plug, so silicone material from the wall was not removed, in contrast to punched holes where wall material is removed. Silicone adhesive behind the restraining plugs was used to fix the restraining plugs in place and the adhesive sealed the ends of the lumen. The slits were placed at 2 to 3 mm from each end of the drug core. A bi-oval shape wireform was inserted into the small lumen of the tube, and silicone adhesive was applied into the small lumen to fix the wireform in place and allowed to cure for approximately 24 hours after which time the ends were trimmed to 5 mm from the end of the restraining plugs. The silicone restraining plugs were oversized; the inner diameter of the silicone tube was 2.64 mm while the outer diameter of the silicone restraining plugs was 2.77 mm. The parylene coating on the restraining plug was used to prevent gamma irradiation induced adhesion at the silicone-to-silicone interface after gamma irradiation was used for product sterilization. A small piece of paper was inserted into each slit to prevent possible adherence and closure of the wall during the irradiation, and then was removed afterward irradiation. The slits over the oversized restraining plugs were designed to serve as drug release outlets as osmotic pressure inside the drug chamber is built up.

The location and the number of slits can vary depending on how many and where restraining plugs are located along the length of the tube. For example, if only one restraining plug is present in the middle of the tube, there can be one slit in the middle of the tube.

Three Opening System (One Laser-Drilled Orifice and Two Plugs).

FIGS. 2 and 3A show a three opening system having a laser-drilled aperture with a 150 micron diameter in the middle of the tube, and two plugs (see FIGS. 3B and 3C), which had the outer diameter of 2.77 mm and the length of 8 mm. The plugs were made of silicone and coated with parylene C, and each plug included a bevel at one end (see FIGS. 3A-3C). Silicone adhesive was applied in the region created by the bevel end and the large lumen to fix the plugs in place but the adhesive did not seal the ends of the lumen. FIGS. 3B and 3C shows one end of the three opening system and the plug is shown. FIGS. 1C and 1D show the diagram of such one-way valve; each plug, oversized in the large lumen, forms one-way valve once osmotic pressure in the large lumen is built up.

Unlike the punched holes over oversized restraining plugs (FIGS. 9A-9B) and the slits over oversized restraining plugs (FIGS. 10A-10B) and the plugs (FIGS. 1C, 1D, 3B, 3C), the laser-drilled hole is an aperture with a pre-defined opening, which is present regardless of the presence of osmotic pressure in the drug reservoir (i.e., the large lumen or drug compartment lumen).

In Vitro Release Testing.

Six types of systems were tested for in vitro release, according to the parameters in Table 3. The shapes of all types of systems were bi-oval. However, the number and configuration of drug release openings, silicone tube wall thickness (RW or TW), and silicone tube hardness (50 A and 35 A) differed depending on system type. All of the systems were gamma irradiated (25-40 kGy) before being tested for in vitro release.

TABLE 3

List of tested systems in in vitro release

| Type | System | Silicone tube |
|---|---|---|
| 1 | Four opening system with four punched holes and RW tube (as in FIGS. 9A-9B) | Regular wall (RW) silicone tube with a large lumen with 2.64 mm ID and 0.20 mm wall, and 50A durometer |
| 2 | Two opening system with two slits and RW tube (as in FIGS. 10A-10B) | |
| 3 | Three opening system with a laser-drilled orifice and two plugs and RW tube (as in FIGS. 2-3) | |
| 4 | Four opening system with four punched holes and TW tube (as in FIGS. 9A-9B) | Thick wall (TW) silicone tube with a large lumen with 2.64 mm ID and 0.41 mm wall, and 35A durometer |
| 5 | Two opening system with two slits and TW tube (as in FIGS. 10A-10B) | |
| 6 | Three opening system with a laser-drilled orifice and two plugs and TW tube (as in FIGS. 2-3) | |

In Vitro Release with 0.20 mm Wall (RW) Tube.

Figure 14:
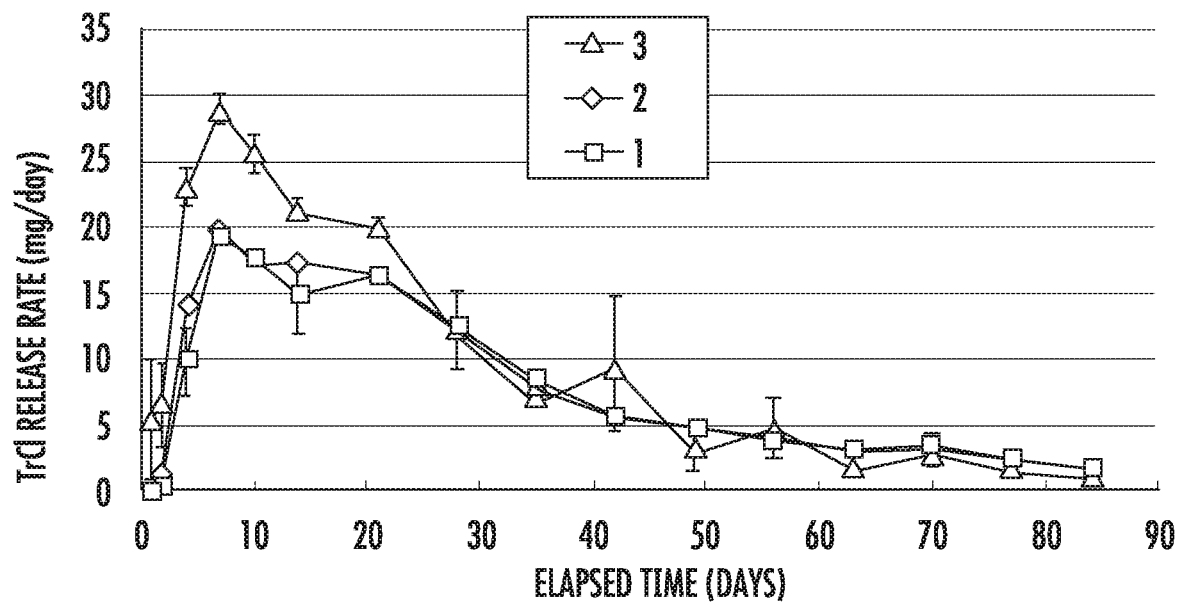
FIG. 14 is a graph showing drug release rate over time for various drug delivery devices tested in the Examples.
Figure 15:
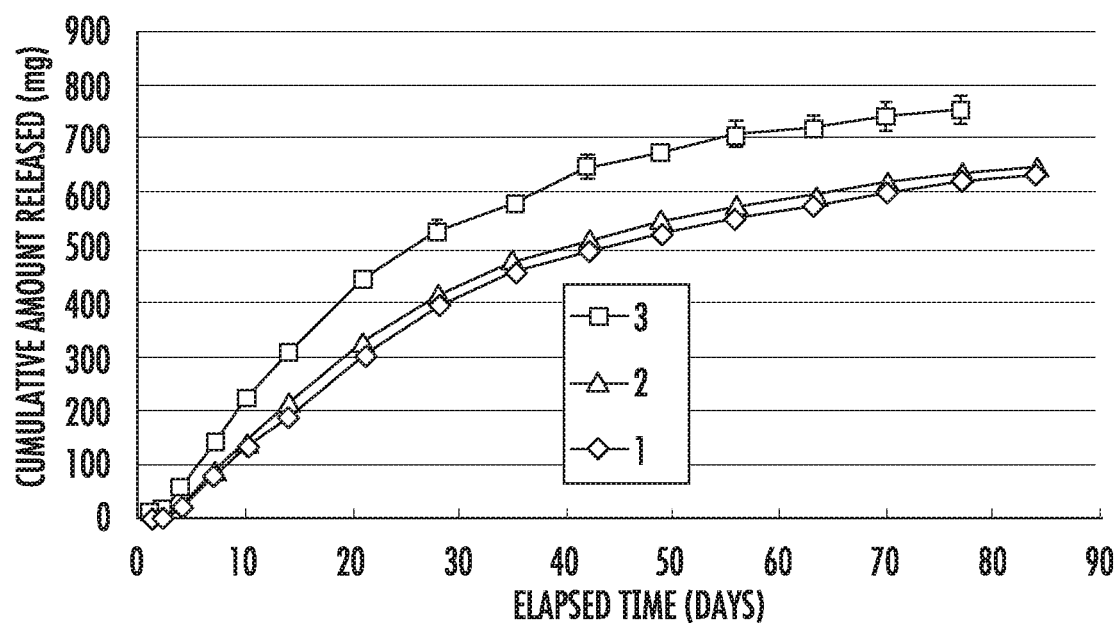
FIG. 15 is a graph showing cumulative drug release over time for various drug delivery devices tested in the Examples.

The systems were placed in 300 grams of deionized water at 37° C., and time point samples were collected at predetermined time points to construct in vitro release profiles. FIGS. 14 and 15 show trospium chloride release rates and cumulative amount released over time for Type 1, 2, and 3 in Table 3. No noticeable difference was observed in the drug release characteristics between two opening systems (with slits) and four opening systems (with punched holes), which supports osmotically controlled drug release. However, the three opening system, which has a pre-defined laser-drilled aperture and two plugs, showed higher overall cumulative release amount compared with two opening systems and four opening systems.

In Vitro Release with 0.41 mm Wall (TW) Tube.

Figure 16:
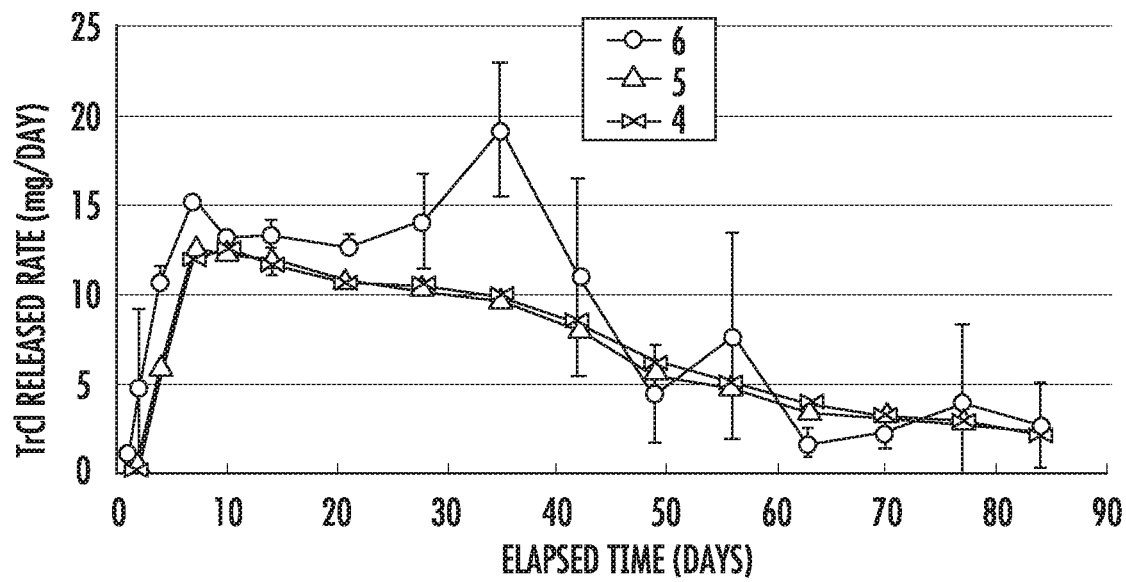
FIG. 16 is a graph showing drug release rate over time for various drug delivery devices tested in the Examples.
Figure 17:
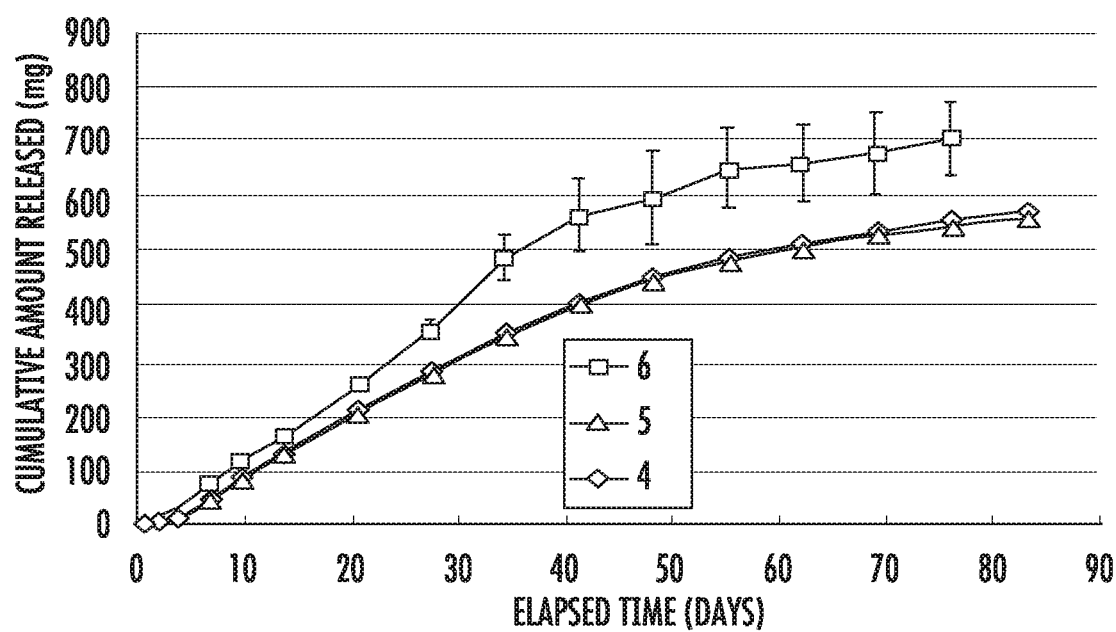
FIG. 17 is a graph showing cumulative drug release over time for various drug delivery devices tested in the Examples.

The systems were placed in 300 grams of deionized water at 37° C., and time point samples were collected at predetermined time points to construct in vitro release profiles. FIGS. 16 and 17 show trospium chloride release rates and cumulative amount released over time for Type 4, 5, and 6 in Table 3. No noticeable difference was observed in the drug release characteristics between two opening systems (with slits) and four opening systems (with punched holes), which supports osmotically controlled drug release. However, three opening system, which has a pre-defined laser-drilled aperture and two plugs, showed higher overall cumulative release amount compared with two opening systems and four opening systems.

Example 5

Devices were manufactured to compare a system having two end restraining plugs and no sidewall orifice (such as disclosed in U.S. Patent Application Publication 2016/0008271 to Lee) with a system having preformed ports in the sidewall adjacent restraining plugs and no sidewall orifice (such as illustrated in FIG. 9). The device parameters are given below in Table 4.

The devices were immersed in deionized water and the release rate of the drug was measured over time. The results are illustrated in FIG. 24, which demonstrates that the system having the punched holes with adjacent restraining plugs to form the microchannels therebetween produces a similar release profile over the 84 day in vitro release test as compared to the prior plug only system. Indeed, the system having punched holes with restraining plugs showed a smoother release profile as compared to the plug only system.

TABLE 4

Device parameters for Example 5

| Sample No. | Drug Constituent | Device Constituent | IVR Conditions |
|---|---|---|---|
| 1 | Emerson Tablets, Lot CU06-050, 95% Tros/PVP Gran (97:3), 5% PEG8K, 2.16 mm OD | 2.16 mm ID × 0.4 mm wall thickness, Thick Wall, 35A, plugs no orifice | 100.00 ± 0.05 g of DI water for the first 14 days and then increased to 300.00 ± 0.05 g of DI water for 84 days. Stored at 37° C. |
| 2 |  | 2.16 mm ID × 0.4 mm wall thickness, thick wall, 35A, 4 punched holes of 0.76 mm diameter each, no orifice | 300.00 ± 0.05 g of DI water for 84 days. Stored at 37° C. |

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

What is claimed is:

1. A drug delivery device comprising:
a body that comprises a wall bounding a reservoir defined within the body, the wall having at least one preformed through-hole disposed in the wall and extending to the reservoir, and the wall comprising a water-permeable portion, the body comprising an elastic portion;
a drug formulation which comprises a drug, the drug formulation being disposed within the reservoir; and
at least one restraining plug, each of the at least one restraining plug closing off a respective opening of the body and contacting the elastic portion of the body, the respective opening being in fluid communication with the reservoir and with the at least one preformed through-hole,
wherein the water-permeable portion of the wall is configured to permit water to enter the drug delivery device and contact the drug formulation located in the reservoir,
wherein release of the drug from the device is controlled by (i) release of the drug through the at least one preformed through-hole in the wall, and (ii) release of the drug through the transient formation of one or more microchannels between the elastic portion of the body and the at least one restraining plug along an inner surface of the elastic portion of the body, extending to the respective opening, upon the generation within the reservoir of a hydrostatic pressure effective to form the one or more microchannels, and
wherein the one or more microchannels are configured to collapse at least partially as the hydrostatic pressure is relieved.

2. The drug delivery device of claim 1, wherein release of the drug through the at least one preformed through-hole is osmotically driven.

3. The drug delivery device of claim 1, wherein:
each of the at least one restraining plug has a respective outer diameter,
the elastic portion of the body defines at least one respective opening having a respective inner diameter, and
the respective outer diameter of each restraining plug exceeds the respective inner diameter of each respective opening of the elastic portion of the body by at least 3 percent.

4. The drug delivery device of claim 3, wherein the respective outer diameter of each of the at least one restraining plug exceeds the respective inner diameter of the respective opening of the elastic portion of the body by at least 5 percent, at least 10 percent, at least 15 percent, at least 20 percent, or at least 25 percent.

5. The drug delivery device of claim 1, wherein the body further comprises an inelastic portion.

6. The drug delivery device of claim 1, wherein the at least one restraining plug is secured within the respective opening in the elastic portion of the body with an adhesive.

7. The drug delivery device of claim 1, wherein the drug formulation is in a solid form.

8. The drug delivery device of claim 7, wherein the device is configured to permit, in vivo, water to diffuse through the water-permeable portion of the wall and into the reservoir to solubilize the solid drug formulation.

9. The drug delivery device of claim 1, wherein the drug comprises trospium or another antimuscarinic agent.

10. The drug delivery device of claim 1, further comprising an osmotic agent.

11. The drug delivery device of claim 10, wherein the osmotic agent is a component of the drug formulation.

12. The drug delivery device of claim 1, wherein the at least one restraining plug is substantially cylindrical.

13. The drug delivery device of claim 1, wherein the at least one restraining plug comprises a wedged, tapered, angled, or rounded surface.

14. The drug delivery device of claim 1, wherein the Shore durometer of the elastic portion of the body is from about 40A to about 60A, and the Shore durometer of the at least one restraining plug is from about 70A to about 100A.

15. The drug delivery device of claim 1, wherein the Shore durometer of the elastic portion of the body is from about 45A to about 55A, and the Shore durometer of the at least one restraining plug is from about 75A to about 85A.

16. The drug delivery device of claim 1, wherein the Shore durometer of the elastic portion of the body is about 50A, and the Shore durometer of the at least one restraining plug is about 80A.

17. The drug delivery device of claim 1, wherein the device is elastically deformable between a relatively straightened shape suitable for insertion through a lumen into a body cavity of a patient and a retention shape suited to retain the device within the body cavity.

18. The drug delivery device of claim 1, wherein the body is formed from an elastomeric tube.

19. The drug delivery device of claim 1, wherein the elastic portion of the body is formed from a water-permeable material.

20. The drug delivery device of claim 1, wherein the at least one restraining plug has a parylene coating.

21. A drug delivery device comprising:
a tubular body that comprises a wall bounding a reservoir defined within the body, the wall comprising a water-permeable portion and an elastic portion having at least one preformed release port disposed in the elastic portion of the wall;
a drug formulation which comprises a drug, the drug formulation being disposed within the reservoir, wherein the water-permeable portion of the wall permits water to enter the drug delivery device and contact the drug formulation located in the reservoir; and
at least one restraining plug secured within the reservoir in contact with the elastic portion of the body and adjacent the at least one preformed release port, such that the at least one restraining plug controls release of the drug from the device, via the at least one preformed release port, by the transient formation of one or more microchannels between the elastic portion of the body and the at least one restraining plug along an inner surface of the elastic portion of the body, extending to the at least one preformed release port, upon the generation of a hydrostatic pressure within the reservoir effective to form the one or more microchannels, and
wherein the one or more microchannels are configured to collapse at least partially as the hydrostatic pressure is relieved, and
wherein the drug delivery device releases drug without degradation of the at least one restraining plug.

22. The drug delivery device of claim 21, wherein the at least one preformed release port comprises a through-hole or a slit disposed in the wall.

23. The drug delivery device of claim 21, wherein:
each of the at least one restraining plug has a respective outer diameter,
the elastic portion of the body defines at least one respective opening having a respective inner diameter, and
the respective outer diameter of each restraining plug exceeds the respective inner diameter of each respective opening of the elastic portion of the body by at least 3 percent.

24. The drug delivery device of claim 23, wherein the respective outer diameter of each of the at least one restraining plug exceeds the respective inner diameter of the respective opening of the elastic portion of the body by at least 5 percent, at least 10 percent, at least 15 percent, at least 20 percent, or at least 25 percent.

25. The drug delivery device of claim 21, wherein the body further comprises an inelastic portion.

26. The drug delivery device of claim 21, wherein the at least one restraining plug is secured within the elastic portion of the body with an adhesive.

27. The drug delivery device of claim 21, wherein the drug formulation is in a solid form.

28. The drug delivery device of claim 27, wherein the device is configured to permit, in vivo, water to diffuse through the water-permeable portion of the wall and into the reservoir to solubilize the solid drug formulation.

29. The drug delivery device of claim 21, wherein the drug comprises trospium or another antimuscarinic agent.

30. The drug delivery device of claim 21, further comprising an osmotic agent.

31. The drug delivery device of claim 30, wherein the osmotic agent is a component of the drug formulation.

32. The drug delivery device of claim 21, wherein the at least one restraining plug is substantially cylindrical.

33. The drug delivery device of claim 21, wherein the Shore durometer of the elastic portion of the body is from about 40A to about 60A, and the Shore durometer of the at least one restraining plug is from about 70A to about 100A.

34. The drug delivery device of claim 21, wherein the Shore durometer of the elastic portion of the body is from about 45A to about 55A, and the Shore durometer of the at least one restraining plug is from about 75A to about 85A.

35. The drug delivery device of claim 21, wherein the Shore durometer of the elastic portion of the body is about 50A, and the Shore durometer of the at least one restraining plug is about 80A.

36. The drug delivery device of claim 21, wherein the device is elastically deformable between a relatively straightened shape suitable for insertion through a lumen into a body cavity of a patient and a retention shape suited to retain the device within the body cavity.

37. The drug delivery device of claim 21, wherein the elastic portion of the body is formed from a water-permeable material.

38. The drug delivery device of claim 21, wherein the at least one restraining plug has a parylene coating.

39. The drug delivery device of claim 21, further comprising at least one preformed through-hole disposed in the wall of the body, wherein release of the drug from the device is further controlled by release of the drug through the at least one preformed through-hole in the wall.

40. The drug delivery device of claim 39, wherein release of the drug through the at least one preformed through-hole is osmotically driven.

41. A drug delivery device comprising:
a water-permeable silicone tube that comprises a wall bounding a reservoir, the wall comprising an elastic portion having four preformed release ports disposed therein;
a solid drug formulation comprising a drug and disposed within the reservoir, wherein the device is configured to permit, in vivo, water to diffuse through the wall and into the reservoir to solubilize the solid drug formulation;
a first restraining plug adhesively secured within the reservoir and in contact with the elastic portion of the body, the first restraining plug being adjacent a first and a second of the four preformed release ports and between the first and the second of the four preformed released ports in a direction across the water-permeable silicone tube; and
a second restraining plug adhesively secured within the reservoir and in contact with the elastic portion of the body, the second restraining plug being adjacent a third and a fourth of the four preformed release ports and between the third and the fourth of the four preformed released ports in a direction across the water-permeable silicone tube,
wherein the device is configured to provide controlled release of the drug from the device via one or more of the first, second, third, and fourth preformed release ports, by the transient formation of one or more microchannels between the elastic portion of the body and one or both of the first and second restraining plugs, along an inner surface of the elastic portion of the body, upon the generation of a hydrostatic pressure within the reservoir effective to form the one or more microchannels.

42. The drug delivery device of claim 41, wherein the four preformed release ports comprise through-holes disposed in the wall.

43. The drug delivery device of claim 41, wherein the drug comprises trospium or another antimuscarinic agent.

44. The drug delivery device of claim 41, wherein the first and second restraining plugs have a parylene coating.

45. The drug delivery device of claim 41, wherein the silicone tube is a dual-lumen tube in which a first lumen includes the reservoir and a second lumen is a retention frame lumen that houses a retention frame.

46. The drug delivery device of claim 45, wherein the device is elastically deformable between a relatively straightened shape suitable for insertion through a lumen into a body cavity of a patient and a retention shape suited to retain the device within the body cavity.

47. The drug delivery device of claim 45, wherein the retention frame is a nitinol wire.

* * * * *